US012703880B2

(12) United States Patent
Huang et al.

(10) Patent No.: US 12,703,880 B2
(45) **Date of Patent: *Aug. 11, 2026**

(54) METHOD FOR ASYMMETRIC AMPLIFICATION OF MULTIPLE TARGET NUCLEIC ACIDS

(71) Applicant: XIAMEN UNIVERSITY, Xiamen (CN)

(72) Inventors: Qiuying Huang, Xiamen (CN); Qingge Li, Xiamen (CN)

(73) Assignee: Xiamen University, Xiamen (CN)

( * ) Notice: Subject to any disclaimer, the term of this patent is extended or adjusted under 35 U.S.C. 154(b) by 1027 days.

This patent is subject to a terminal disclaimer.

(21) Appl. No.: 17/757,982

(22) PCT Filed: Jul. 22, 2020

(86) PCT No.: PCT/CN2020/103412

§ 371 (c)(1),
(2) Date: Jun. 24, 2022

(87) PCT Pub. No.: WO2021/128823

PCT Pub. Date: Jul. 1, 2021

(65) Prior Publication Data

US 2022/0364146 A1 Nov. 17, 2022

(30) Foreign Application Priority Data

Dec. 26, 2019 (CN) ......................... 201911367142.0

(51) Int. Cl.

| | |
|---|---|
| ***C12Q 1/686*** | (2018.01) |
| ***C12Q 1/6818*** | (2018.01) |
| ***C12Q 1/6848*** | (2018.01) |
| ***C12Q 1/6853*** | (2018.01) |

(52) U.S. Cl.
CPC .......... *C12Q 1/686* (2013.01); *C12Q 1/6818* (2013.01); *C12Q 1/6848* (2013.01); *C12Q 1/6853* (2013.01)

(58) Field of Classification Search
CPC ................. C12Q 1/686; C12Q 1/6844; C12Q 2527/143; C12Q 1/6853
See application file for complete search history.

(56) References Cited

U.S. PATENT DOCUMENTS

2003/0108900 A1 6/2003 Oliphant et al.
2004/0214196 A1 10/2004 Aydin
(Continued)

FOREIGN PATENT DOCUMENTS

CN 1629305 A 6/2005
CN 1688718 A 10/2005
(Continued)

OTHER PUBLICATIONS

European Search Report for application EP 20 90 5335, mailed Jan. 30, 2024, pp. 1-3. (Year: 2024).*
(Continued)

*Primary Examiner* — Young J Kim
(74) *Attorney, Agent, or Firm* — Medler Ferro Woodhouse & Mills PLLC

(57) ABSTRACT

Provided is multiplex and asymmetric amplification of nucleic acid molecules. In particular, provided is a method for simultaneous and asymmetric amplification of one or more target nucleic acids in a sample. The method can simultaneously and asymmetrically amplify multiple target nucleic acids existing in a sample, and can simultaneously produce large number of single stranded products.

19 Claims, 6 Drawing Sheets

Specification includes a Sequence Listing.

(56) References Cited

U.S. PATENT DOCUMENTS

| | | | | |
|---|---|---|---|---|
| 2010/0151448 | A1 | 6/2010 | Zhang et al. | |
| 2019/0153508 | A1 | 5/2019 | Smit et al. | |
| 2020/0140931 | A1 | 5/2020 | Li et al. | |
| 2024/0076739 | A1 * | 3/2024 | Li ........................ | C12Q 1/6851 |

FOREIGN PATENT DOCUMENTS

| | | | |
|---|---|---|---|
| CN | 106566871 | A | 4/2017 |
| CN | 106795569 | A | 5/2017 |
| CN | 107177688 | A | 9/2017 |
| CN | 107338315 | A | 11/2017 |
| CN | 108823287 | A | 11/2018 |
| EP | 4083220 | A1 | 11/2022 |
| EP | 4083224 | A1 | 11/2022 |
| JP | 2008-510471 | A | 4/2008 |
| JP | 2015-536653 | A | 12/2015 |
| WO | 2013/128281 | A1 | 9/2013 |
| WO | 2017/007586 | A1 | 1/2017 |
| WO | 2019/101796 | A1 | 5/2019 |
| WO | 2020/010124 | A2 | 1/2020 |
| WO | 2021/128860 | A1 | 7/2021 |

OTHER PUBLICATIONS

D'Auriac, "COMplementary primer ASymmetric PCR (Compas-PCR) applied to the identification of *Salmo salar, Salmo trutta* and Their Hybrids," PLoS One 11(10):e0165468 (2016).

Liu and Chen, "High-efficiency thermal asymmetric interlaced PCR for amplification of unknown flanking sequences," Bio Techniques 43(5):649-656 (2007).

Zhang et al., "Sensitive Detection of SARS Coronavirus RNA by a Novel Asymmetric Multiplex Nested RT-PCT Amplification Coupled with Oligonucleotide Microarray Hybridization," 114: 59-78 (2005).

Zhu et al., "Multiplex Asymmetric PCR-Based Oligonucleotide Microarray for Detection of Drug Resistance Genes Containing Single Mutations in *Enterobacteriaceae*," Antimicrobial Agents and Chemotherapy 51(10):3707-3713 (2007).

English translation of the International Search Report in PCT/CN2020/103412, dated Oct. 27, 2020.

English translation of the International Search Report in PCT/CN2020/107308, mailed Nov. 12, 2020.

Brownie et al., "The Elimination of Primer-dimer Accumulation in PCR," *Nucleic Acids Research* 25(16):3235-3241 (1997).

Huang et al., "Multicolor combinatorial probe coding for real-time PCR," *PLoS One* 6(1):e16033 (2011).

Liu et al., "Multiplex detection and genotyping of pathogenic bacteria on paper-based biosensor with a novel universal primer mediated asymmetric PCR," *Biosensors and Bioelectronics* 74:778-785 (2015).

Wang et al., "An Oligonucleotide Microarray Coupled with Universal Primer-Multiplex Asymmetric PCR for Detection of Seven Foodborne Pathogens," *Food Science* 38(8):290-295 (2017), English Abstract.

Non-Final Office Action in U.S. Appl. No. 17/757,986, dated Oct. 27, 2025.

* cited by examiner

SEQUENCE LISTING

```
<160> NUMBER OF SEQ ID NOS: 51

<210> SEQ ID NO 1
<211> LENGTH: 38
<212> TYPE: DNA
<213> ORGANISM: Artificial sequence
<220> FEATURE:
<223> OTHER INFORMATION: rs8027171-F

<400> SEQUENCE: 1

tcgcaagcac tcacgtagag caagtgcagg tggagaca                              38


<210> SEQ ID NO 2
<211> LENGTH: 43
<212> TYPE: DNA
<213> ORGANISM: Artificial sequence
```

```
<220> FEATURE:
<223> OTHER INFORMATION: rs8027171-R

<400> SEQUENCE: 2

gtcgcaagca ctcacgtaga gagtcgtggc taaaggatag aac                    43


<210> SEQ ID NO 3
<211> LENGTH: 20
<212> TYPE: DNA
<213> ORGANISM: Artificial sequence
<220> FEATURE:
<223> OTHER INFORMATION: Tag 1 primer

<400> SEQUENCE: 3

tcgcaagcac tcacgtagag                                              20


<210> SEQ ID NO 4
<211> LENGTH: 22
<212> TYPE: DNA
<213> ORGANISM: Artificial sequence
<220> FEATURE:
<223> OTHER INFORMATION: Tag 2 primer

<400> SEQUENCE: 4

gtcgcaagca ctcacgtaga ga                                           22


<210> SEQ ID NO 5
<211> LENGTH: 26
<212> TYPE: DNA
<213> ORGANISM: Artificial sequence
<220> FEATURE:
<223> OTHER INFORMATION: rs8027171-P

<400> SEQUENCE: 5

atcggataga aaacatggag accgat                                       26


<210> SEQ ID NO 6
<211> LENGTH: 47
<212> TYPE: DNA
<213> ORGANISM: Artificial sequence
<220> FEATURE:
<223> OTHER INFORMATION: rs48189298-F

<400> SEQUENCE: 6

gtcgcaagca ctcacgtaga ggaaatttca gaattgttat ggaccag                47


<210> SEQ ID NO 7
<211> LENGTH: 38
<212> TYPE: DNA
<213> ORGANISM: Artificial sequence
<220> FEATURE:
<223> OTHER INFORMATION: rs48189298-R

<400> SEQUENCE: 7

gtcgcaagca ctcacgtaga gacagaggca ggtcgtct                          38


<210> SEQ ID NO 8
<211> LENGTH: 40
<212> TYPE: DNA
<213> ORGANISM: Artificial sequence
<220> FEATURE:
<223> OTHER INFORMATION: rs60871880-F

<400> SEQUENCE: 8

gtcgcaagca ctcacgtaga gcaggcccaa atccattctc                        40
```

<210> SEQ ID NO 9
<211> LENGTH: 38
<212> TYPE: DNA
<213> ORGANISM: Artificial sequence
<220> FEATURE:
<223> OTHER INFORMATION: rs60871880-R

<400> SEQUENCE: 9
gtcgcaagca ctcacgtaga gatcaagagg cacagcca 38

<210> SEQ ID NO 10
<211> LENGTH: 21
<212> TYPE: DNA
<213> ORGANISM: Artificial sequence
<220> FEATURE:
<223> OTHER INFORMATION: Tag 3 primer

<400> SEQUENCE: 10
gtcgcaagca ctcacgtaga g 21

<210> SEQ ID NO 11
<211> LENGTH: 30
<212> TYPE: DNA
<213> ORGANISM: Artificial sequence
<220> FEATURE:
<223> OTHER INFORMATION: rs48189298-P

<400> SEQUENCE: 11
atgctctatg tgttcaattt gttccgagca 30

<210> SEQ ID NO 12
<211> LENGTH: 33
<212> TYPE: DNA
<213> ORGANISM: Artificial sequence
<220> FEATURE:
<223> OTHER INFORMATION: rs60871880-P

<400> SEQUENCE: 12
tgtgctgaag ctaagagcaa agggggccag cac 33

<210> SEQ ID NO 13
<211> LENGTH: 43
<212> TYPE: DNA
<213> ORGANISM: Artificial sequence
<220> FEATURE:
<223> OTHER INFORMATION: rs4847034-F

<400> SEQUENCE: 13
tcgcaagcac tcacgtagag tggtaatttg aattcctttg ggt 43

<210> SEQ ID NO 14
<211> LENGTH: 39
<212> TYPE: DNA
<213> ORGANISM: Artificial sequence
<220> FEATURE:
<223> OTHER INFORMATION: rs4847034-R

<400> SEQUENCE: 14
gtcgcaagca ctcacgtaga gaggtgcagc tatggcaga 39

<210> SEQ ID NO 15
<211> LENGTH: 44
<212> TYPE: DNA
<213> ORGANISM: Artificial sequence
<220> FEATURE:
<223> OTHER INFORMATION: rs2826949-F

<400> SEQUENCE: 15
tcgcaagcac tcacgtagag tgtcatcata ctaatgccta tgtc 44

<210> SEQ ID NO 16
<211> LENGTH: 50
<212> TYPE: DNA
<213> ORGANISM: Artificial sequence
<220> FEATURE:
<223> OTHER INFORMATION: rs2826949-R

<400> SEQUENCE: 16
gtcgcaagca ctcacgtaga gaattaaagg ttcaaataag taattactgt 50

<210> SEQ ID NO 17
<211> LENGTH: 37
<212> TYPE: DNA
<213> ORGANISM: Artificial sequence
<220> FEATURE:
<223> OTHER INFORMATION: rs8103778-F

<400> SEQUENCE: 17
tcgcaagcac tcacgtagag ttggtccctg gctctgt 37

<210> SEQ ID NO 18
<211> LENGTH: 42
<212> TYPE: DNA
<213> ORGANISM: Artificial sequence
<220> FEATURE:
<223> OTHER INFORMATION: rs8103778-R

<400> SEQUENCE: 18
gtcgcaagca ctcacgtaga gatgagctga gcttgggata tg 42

<210> SEQ ID NO 19
<211> LENGTH: 49
<212> TYPE: DNA
<213> ORGANISM: Artificial sequence
<220> FEATURE:
<223> OTHER INFORMATION: rs1396009-F

<400> SEQUENCE: 19
tcgcaagcac tcacgtagag ttgtgaactt tactacataa tctaaggaa 49

<210> SEQ ID NO 20
<211> LENGTH: 48
<212> TYPE: DNA
<213> ORGANISM: Artificial sequence
<220> FEATURE:
<223> OTHER INFORMATION: rs1396009-R

<400> SEQUENCE: 20
gtcgcaagca ctcacgtaga gatttacttt tacgtagttt ttactcca 48

<210> SEQ ID NO 21
<211> LENGTH: 44
<212> TYPE: DNA
<213> ORGANISM: Artificial sequence
<220> FEATURE:
<223> OTHER INFORMATION: rs1523537-F

<400> SEQUENCE: 21
tcgcaagcac tcacgtagag taagcccttt catattttat gcct 44

<210> SEQ ID NO 22

<211> LENGTH: 46
<212> TYPE: DNA
<213> ORGANISM: Artificial sequence
<220> FEATURE:
<223> OTHER INFORMATION: rs1523537-R

<400> SEQUENCE: 22
gtcgcaagca ctcacgtaga gattcataat acaacctgtc tttgga 46

<210> SEQ ID NO 23
<211> LENGTH: 45
<212> TYPE: DNA
<213> ORGANISM: Artificial sequence
<220> FEATURE:
<223> OTHER INFORMATION: rs1528460-F

<400> SEQUENCE: 23
gtcgcaagca ctcacgtaga gacttcctcc tggagatcaa tattt 45

<210> SEQ ID NO 24
<211> LENGTH: 40
<212> TYPE: DNA
<213> ORGANISM: Artificial sequence
<220> FEATURE:
<223> OTHER INFORMATION: rs1528460-R

<400> SEQUENCE: 24
tcgcaagcac tcacgtagag tgattatgtt gggatggggt 40

<210> SEQ ID NO 25
<211> LENGTH: 43
<212> TYPE: DNA
<213> ORGANISM: Artificial sequence
<220> FEATURE:
<223> OTHER INFORMATION: rs7937238-F

<400> SEQUENCE: 25
gtcgcaagca ctcacgtaga gatcagtctg atttaggtgt gtc 43

<210> SEQ ID NO 26
<211> LENGTH: 41
<212> TYPE: DNA
<213> ORGANISM: Artificial sequence
<220> FEATURE:
<223> OTHER INFORMATION: rs7937238-R

<400> SEQUENCE: 26
tcgcaagcac tcacgtagag ttaggagatg ttgtcatggc a 41

<210> SEQ ID NO 27
<211> LENGTH: 40
<212> TYPE: DNA
<213> ORGANISM: Artificial sequence
<220> FEATURE:
<223> OTHER INFORMATION: rs2111980-F

<400> SEQUENCE: 27
gtcgcaagca ctcacgtaga gacggtcaaa gcatcttggc 40

<210> SEQ ID NO 28
<211> LENGTH: 41
<212> TYPE: DNA
<213> ORGANISM: Artificial sequence
<220> FEATURE:
<223> OTHER INFORMATION: rs2111980-R

<400> SEQUENCE: 28
tcgcaagcac tcacgtagag tacaaactga tcctatgcag c 41

<210> SEQ ID NO 29
<211> LENGTH: 42
<212> TYPE: DNA
<213> ORGANISM: Artificial sequence
<220> FEATURE:
<223> OTHER INFORMATION: rs7278737-F

<400> SEQUENCE: 29
tcgcaagcac tcacgtagag ctttggtgta catgtgtttg ga 42

<210> SEQ ID NO 30
<211> LENGTH: 43
<212> TYPE: DNA
<213> ORGANISM: Artificial sequence
<220> FEATURE:
<223> OTHER INFORMATION: rs7278737-R

<400> SEQUENCE: 30
gtcgcaagca ctcacgtaga gagagagaag gaaatcaact ctg 43

<210> SEQ ID NO 31
<211> LENGTH: 41
<212> TYPE: DNA
<213> ORGANISM: Artificial sequence
<220> FEATURE:
<223> OTHER INFORMATION: rs591173-F

<400> SEQUENCE: 31
tcgcaagcac tcacgtagag caaacacatc tcagtgctga c 41

<210> SEQ ID NO 32
<211> LENGTH: 45
<212> TYPE: DNA
<213> ORGANISM: Artificial sequence
<220> FEATURE:
<223> OTHER INFORMATION: rs591173-R

<400> SEQUENCE: 32
gtcgcaagca ctcacgtaga gacatagtgt ttccatgtga atgta 45

<210> SEQ ID NO 33
<211> LENGTH: 48
<212> TYPE: DNA
<213> ORGANISM: Artificial sequence
<220> FEATURE:
<223> OTHER INFORMATION: rs1358856-F

<400> SEQUENCE: 33
gtcgcaagca ctcacgtaga gagcaaatag agttatttca tcatggta 48

<210> SEQ ID NO 34
<211> LENGTH: 43
<212> TYPE: DNA
<213> ORGANISM: Artificial sequence
<220> FEATURE:
<223> OTHER INFORMATION: rs1358856-R

<400> SEQUENCE: 34
tcgcaagcac tcacgtagag gtatttaatt ttgctggcag tgt 43

<210> SEQ ID NO 35
<211> LENGTH: 39
<212> TYPE: DNA

<213> ORGANISM: Artificial sequence
<220> FEATURE:
<223> OTHER INFORMATION: rs2730648-F

<400> SEQUENCE: 35
tcgcaagcac tcacgtagag tcttacctcc agagcctgt 39

<210> SEQ ID NO 36
<211> LENGTH: 44
<212> TYPE: DNA
<213> ORGANISM: Artificial sequence
<220> FEATURE:
<223> OTHER INFORMATION: rs2730648-R

<400> SEQUENCE: 36
gtcgcaagca ctcacgtaga gataccagaa ctattgaagg catc 44

<210> SEQ ID NO 37
<211> LENGTH: 38
<212> TYPE: DNA
<213> ORGANISM: Artificial sequence
<220> FEATURE:
<223> OTHER INFORMATION: rs859400-F

<400> SEQUENCE: 37
gtcgcaagca ctcacgtaga gagccaactg ctgccaag 38

<210> SEQ ID NO 38
<211> LENGTH: 40
<212> TYPE: DNA
<213> ORGANISM: Artificial sequence
<220> FEATURE:
<223> OTHER INFORMATION: rs859400-R

<400> SEQUENCE: 38
tcgcaagcac tcacgtagag ttgttcactc tccctctctg 40

<210> SEQ ID NO 39
<211> LENGTH: 31
<212> TYPE: DNA
<213> ORGANISM: Artificial sequence
<220> FEATURE:
<223> OTHER INFORMATION: rs4847034-P

<400> SEQUENCE: 39
tccgttttat ttttagtttg tttagaaacg g 31

<210> SEQ ID NO 40
<211> LENGTH: 38
<212> TYPE: DNA
<213> ORGANISM: Artificial sequence
<220> FEATURE:
<223> OTHER INFORMATION: rs2826949-P

<400> SEQUENCE: 40
cagatggagt ggtcaaattt agtcctaagt aaccatct 38

<210> SEQ ID NO 41
<211> LENGTH: 33
<212> TYPE: DNA
<213> ORGANISM: Artificial sequence
<220> FEATURE:
<223> OTHER INFORMATION: rs8103778-P

<400> SEQUENCE: 41
tcgggacccc ggcaccacca ccaagccatc ccg 33

<210> SEQ ID NO 42
<211> LENGTH: 24
<212> TYPE: DNA
<213> ORGANISM: Artificial sequence
<220> FEATURE:
<223> OTHER INFORMATION: rs1396009-P

<400> SEQUENCE: 42
tcgcagaaga aaaacatact tgcg 24

<210> SEQ ID NO 43
<211> LENGTH: 34
<212> TYPE: DNA
<213> ORGANISM: Artificial sequence
<220> FEATURE:
<223> OTHER INFORMATION: rs1523537-P

<400> SEQUENCE: 43
cggccaagat cttgtaggga cgctatcgct ggcc 34

<210> SEQ ID NO 44
<211> LENGTH: 25
<212> TYPE: DNA
<213> ORGANISM: Artificial sequence
<220> FEATURE:
<223> OTHER INFORMATION: rs1528460-P

<400> SEQUENCE: 44
tgccagtctt aaatatgtta aggca 25

<210> SEQ ID NO 45
<211> LENGTH: 26
<212> TYPE: DNA
<213> ORGANISM: Artificial sequence
<220> FEATURE:
<223> OTHER INFORMATION: rs7937238-P

<400> SEQUENCE: 45
tcccagcagt tcggttgact ttggga 26

<210> SEQ ID NO 46
<211> LENGTH: 35
<212> TYPE: DNA
<213> ORGANISM: Artificial sequence
<220> FEATURE:
<223> OTHER INFORMATION: rs2111980-P

<400> SEQUENCE: 46
cgcggaggca ccaggctgga gctcgaagga tccgc 35

<210> SEQ ID NO 47
<211> LENGTH: 26
<212> TYPE: DNA
<213> ORGANISM: Artificial sequence
<220> FEATURE:
<223> OTHER INFORMATION: rs7278737-P

<400> SEQUENCE: 47
ccgaaacact tcctctctgt cttcgg 26

<210> SEQ ID NO 48
<211> LENGTH: 33
<212> TYPE: DNA
<213> ORGANISM: Artificial sequence
<220> FEATURE:

-continued

```
<223> OTHER INFORMATION: rs591173-P

<400> SEQUENCE: 48

tacgctgtcc taagcacggg aacagataca gcg                                    33


<210> SEQ ID NO 49
<211> LENGTH: 25
<212> TYPE: DNA
<213> ORGANISM: Artificial sequence
<220> FEATURE:
<223> OTHER INFORMATION: rs1358856-P

<400> SEQUENCE: 49

tctgtgtaca tagctgtttg tacat                                             25


<210> SEQ ID NO 50
<211> LENGTH: 30
<212> TYPE: DNA
<213> ORGANISM: Artificial sequence
<220> FEATURE:
<223> OTHER INFORMATION: rs2730648-P

<400> SEQUENCE: 50

tcccttgcta aggaacatga ggataaggga                                        30


<210> SEQ ID NO 51
<211> LENGTH: 35
<212> TYPE: DNA
<213> ORGANISM: Artificial sequence
<220> FEATURE:
<223> OTHER INFORMATION: rs859400-P

<400> SEQUENCE: 51

tgagtcctga gaccacgctg cgagctcccg gactc                                  35
```

METHOD FOR ASYMMETRIC AMPLIFICATION OF MULTIPLE TARGET NUCLEIC ACIDS

REFERENCE TO AN ELECTRONIC SEQUENCE LISTING

The contents of the sequence listing (0199-XU07US1-SEQ Listing.txt; Size: 9 KB; and Date of Creation: Jun. 17, 2022) is herein incorporated by reference in its entirety.

TECHNICAL FIELD

The present application relates to multiplex, asymmetric amplification of nucleic acid molecules. In particular, the present application provides a method for simultaneously and asymmetrically amplifying one or more target nucleic acids in a sample, the method can simultaneously and asymmetrically amplify multiple target nucleic acids present in the sample, and can simultaneously generate a large amount of single-stranded products.

BACKGROUND ART

Asymmetric PCR, first described by Gyllensten et al. (Proc. Natl. Acad. Sci. USA 1988, 85: 7652-7656), refers to a method for generating large amounts of single-stranded DNA (ssDNA) using unequal amounts of a pair of primers. Single-stranded DNA produced by asymmetric PCR can be used for sequencing, used as probes, or to improve detection signals in real-time PCR, microarray detection, and probe melting curve analysis. However, traditional asymmetric PCR often requires careful optimization to maximize the production of specific single-stranded product and minimize the non-specific amplification. When multiple target nucleic acid sequences need to be asymmetrically amplified at the same time, the increase of primer pairs leads to the increase of non-specific amplification such as primer-dimers, which further increases the difficulty of design and optimization.

In traditional asymmetric PCR amplification, due to the reduction of limiting primer concentration, its melting point is lower than the annealing temperature of the PCR reaction, which in turn leads to the inefficiency of asymmetric PCR amplification. In response to this, Sanchez et al., (Proc. Natl. Acad. Sci. USA 2004, 101: 1933-1938) proposed LATE-PCR (Linear-After-The-Exponential-PCR), in which when designing primers, the actual primer concentration is used as a factor affecting the primer melting point ($T_m$) value, and it is expected that the $T_m$ of the low-concentration limiting primers could be increased and thus higher than the annealing temperature, thereby improving the amplification efficiency of asymmetric PCR to generate large amounts of single-stranded products. This method solves the problem of low amplification efficiency of asymmetric PCR and makes asymmetric PCR easier to optimize. However, this method fails to solve the problem of increased non-specific amplification caused by the increase of primer pairs, and thus it is still difficult to achieve multiplex asymmetric PCR amplification.

Brownie et al. (Nucleic Acids Research 1997, 26:3235-3241) describe a Homo-Tag Assisted Non-Dimer System (HAND System). In this system, the same tag sequence is added to the 5' ends of both target-specific upstream and downstream primers to form tailed/tagged target-specific primers. In PCR amplification, the initial PCR amplification is first initiated by a low concentration of tailed/tagged specific primers at a lower annealing temperature; after several cycles, at an elevated annealing temperature, a high concentration of universal primer is used to perform subsequent amplification of the amplification products of the initial PCR amplification. Since the specific primers all contain the same tag sequence, all products (including primer-dimers) produced by the initial PCR amplification have complementary tag sequences at their ends. Due to the high local concentration, the single strands of small fragment products such as primer-dimers are prone to self-annealing to form a stable "pan-handle" structure, preventing the further annealing of universal primers, thereby inhibiting the amplification of primer-dimers. By combining the use of low concentrations of homologously tagged target-specific primers and high concentrations of universal primers, the HAND system can effectively inhibit the amplification of primer-dimers, achieve efficient multiplex PCR amplification, and maintain high amplification efficiency and detection sensitivity. However, the PCR amplification using the HAND system is a symmetric amplification, and cannot produce single-stranded products, which limits the application of the HAND system in the technical fields of gene chips and probe melting curve analysis.

Therefore, it is necessary to develop a new method that can asymmetrically amplify multiple target nucleic acids at the same time, which can realize efficient multiplex PCR amplification and asymmetric PCR amplification at the same time, so as to meet the clinical requirements for the simultaneous amplification and detection of multiple target nucleic acids.

CONTENTS OF THE PRESENT INVENTION

In the present application, unless otherwise specified, the scientific and technical terms used herein have the meanings commonly understood by those skilled in the art. In addition, the nucleic acid chemistry laboratory operation steps used herein are all routine steps widely used in the corresponding fields. Meanwhile, for a better understanding of the present invention, definitions and explanations of related terms are provided below.

As used herein, the terms "target nucleic acid sequence", "target nucleic acid" and "target sequence" refer to a target nucleic acid or sequence thereof to be detected. In the present application, the terms "target nucleic acid sequence", "target nucleic acid" and "target sequence" have the same meaning and are used interchangeably.

As used herein, the terms "target nucleic acid-specific sequence" and "target-specific sequence" refer to a sequence capable of selectively/specifically hybridizing or annealing to a target nucleic acid under conditions allowing the hybridization, annealing or amplification of the nucleic acid, and comprise a sequence complementary to the target nucleic acid sequence. In the present application, the terms "target nucleic acid-specific sequence" and "target-specific sequence" have the same meaning and are used interchangeably. It is readily understood that a target nucleic acid-specific sequence or target-specific sequence is specific for the target nucleic acid. In other words, a target nucleic acid-specific sequence or target-specific sequence is capable of hybridizing or annealing only to a particular target nucleic acid and not to other nucleic acid sequences under conditions allowing the hybridization, annealing, or amplification of nucleic acids. For example, in the present application, "target nucleic acid-specific forward nucleotide sequence" refers to a forward nucleic acid capable of selectively/specifically hybridizing or annealing to a target nucleic acid under conditions that allow the hybridization, annealing or amplification of the nucleic acid, and comprises a sequence complementary to the target nucleic acid.

As used herein, the term "complementary" means that two nucleic acid sequences are capable of forming a hydrogen bond with each other according to the principle of base pairing (Watson-Crick principle), and thereby forming a duplex. In the present application, the term "complementary" comprises "substantially complementary" and "completely complementary". As used herein, the term "completely complementary" means that every base in one nucleic acid sequence is capable of pairing with bases in another nucleic acid strand without mismatch or gap. As used herein, the term "substantially complementary" means that a majority of bases in one nucleic acid sequence are capable of pairing with bases in another nucleic acid strand, which allows the existence of a mismatch or gap (e.g., mismatch or gap of one or more nucleotides). Typically, two nucleic acid sequences that are "complementary" (e.g., substantially complementary or completely complementary) will selectively/specifically hybridize or anneal under conditions that allow the hybridization, annealing or amplification of nucleic acids, and form a duplex. Accordingly, the term "non-complementary" means that two nucleic acid sequences cannot hybridize or anneal under conditions that allow the hybridization, annealing or amplification of nucleic acids to form a duplex. As used herein, the term "not completely complementary" means that bases in one nucleic acid sequence cannot completely pair with bases in another nucleic acid strand, and at least one mismatch or gap exists.

As used herein, the terms "hybridization" and "annealing" refers to the process by which complementary single-stranded nucleic acid molecules form a double-stranded nucleic acid. In the present application, "hybridization" and "annealing" have the same meaning and are used interchangeably. Typically, two nucleic acid sequences that are completely complementary or substantially complementary can hybridize or anneal. The complementarity required for hybridization or annealing of two nucleic acid sequences depends on the hybridization conditions used, in particular the temperature.

As used herein, "conditions allowing nucleic acid hybridization" have the meaning commonly understood by those skilled in the art, and can be determined by conventional methods. For example, two nucleic acid molecules having complementary sequences can hybridize under suitable hybridization conditions. Such hybridization conditions may involve factors such as temperature, pH, composition and ionic strength of the hybridization buffer, etc., and may be determined based on the length and GC content of the two nucleic acid molecules that are complementary. For example, lowly stringent hybridization conditions can be used when the lengths of the two complementary nucleic acid molecules are relatively short and/or the GC content is relatively low. Highly stringent hybridization conditions can be used when the lengths of the two complementary nucleic acid molecules are relatively long and/or the GC content is relatively high. Such hybridization conditions are well known to those skilled in the art, and can be found in, for example, Joseph Sambrook, et al., Molecular Cloning, A Laboratory Manual, Cold Spring Harbor Laboratory Press, Cold Spring Harbor, NY (2001); and M L M Anderson, Nucleic Acid Hybridization, Springer-Verlag New York Inc. NY (1999). In the present application, "hybridization" and "annealing" have the same meaning and are used interchangeably. Accordingly, the expressions "conditions allowing nucleic acid hybridization" and "conditions allowing nucleic acid annealing" also have the same meaning and are used interchangeably.

As used herein, the expression "conditions allowing nucleic acid amplification" has the meaning commonly understood by those skilled in the art, which refers to conditions under which a nucleic acid polymerase (e.g., DNA polymerase) is allowed to use one nucleic acid strand as a template to synthesize another nucleic acid chain and form a duplex. Such conditions are well known to those skilled in the art and may relate to factors such as temperature, pH, composition, concentration and ionic strength of the hybridization buffer, among others. Suitable nucleic acid amplification conditions can be determined by routine methods (see, for example, Joseph Sambrook, et al., Molecular Cloning, A Laboratory Manual, Cold Spring Harbor Laboratory Press, Cold Spring Harbor, N.Y. (2001)). In the method of the present invention, "conditions allowing nucleic acid amplification" are preferably working conditions of a nucleic acid polymerase (e.g., DNA polymerase).

As used herein, the expression "conditions allowing a nucleic acid polymerase to carry out an extension reaction" has the meaning commonly understood by those skilled in the art, which refers to conditions under which a nucleic acid polymerase (e.g., a DNA polymerase) is allowed to use a nucleic acid strand as a template to extend another nucleic acid strand (such as a primer or probe), and to form a duplex. Such conditions are well known to those skilled in the art and may relate to factors such as temperature, pH, composition, concentration and ionic strength of the hybridization buffer, among others. Suitable nucleic acid amplification conditions can be determined by routine methods (see, for example, Joseph Sambrook, et al., Molecular Cloning, A Laboratory Manual, Cold Spring Harbor Laboratory Press, Cold Spring Harbor, N.Y. (2001)). In the method of the present invention, "conditions allowing a nucleic acid polymerase to carry out an extension reaction" are preferably working conditions of a nucleic acid polymerase (e.g., DNA polymerase). In the present application, the expressions "conditions allowing a nucleic acid polymerase to carry out an extension reaction" and "conditions allowing nucleic acid extension" have the same meaning and are used interchangeably.

The working conditions of various enzymes can be determined by those skilled in the art by routine methods, and can generally involve the following factors: temperature, pH of buffer, composition, concentration, ionic strength, and the like. Alternatively, conditions recommended by the manufacturer of enzyme can be used.

As used herein, the term "nucleic acid denaturation" has the meaning commonly understood by those skilled in the art, and refers to a process by which a double-stranded nucleic acid molecule is dissociated into single strands. The expression "conditions allowing nucleic acid denaturation" refers to conditions under which a double-stranded nucleic acid molecule is dissociated into single strands. Such conditions can be conventionally determined by those skilled in the art (see, for example, Joseph Sambrook, et al., Molecular Cloning, A Laboratory Manual, Cold Spring Harbor Laboratory Press, Cold Spring Harbor, N.Y. (2001)). For example, a nucleic acid can be denatured by conventional techniques such as heating, alkali treatment, urea treatment, enzymatic method (e.g., method using helicase). In the present application, the nucleic acid is preferably denatured under heating. For example, a nucleic acid can be denatured by heating to 80-105° C.

As used herein, the term "PCR reaction" has the meaning commonly understood by those skilled in the art, which refers to a reaction (polymerase chain reaction) that amplifies a target nucleic acid using a nucleic acid polymerase and primers. As used herein, the term "multiplex amplification" refers to the amplification of multiple target nucleic acids in the same reaction system. As used herein, the term "asymmetric amplification" refers to that in the amplification product obtained by amplifying a target nucleic acid, the amounts of two complementary nucleic acid strands are different, and the amount of one nucleic acid strand is greater than that of the other nucleic acid strand.

As used herein, and as commonly understood by those of skill in the art, the terms "forward" and "reverse" are used only for convenience in describing and distinguishing two primers in a primer pair; they are relative, and does not have a special meaning.

As used herein, the term "fluorescent probe" refers to an oligonucleotide that carries a fluorescent group and is capable of generating a fluorescent signal.

As used herein, the term "melting curve analysis" has the meaning commonly understood by those skilled in the art and refers to a method for the analysis of the presence or identity of a double-stranded nucleic acid molecule by determining the melting curve of the double-stranded nucleic acid molecule, which is commonly used to assess the dissociation characteristics of double-stranded nucleic acid molecules during heating. Methods for performing melting curve analysis are well known to those skilled in the art (see, for example, The Journal of Molecular Diagnostics 2009, 11(2): 93-101). In the present application, the terms "melting curve analysis" and "melting analysis" have the same meaning and are used interchangeably.

In certain preferred embodiments of the present application, the melting curve analysis can be performed using a detection probe labeled with a reporter group and a quencher group. Briefly, at ambient temperature, the detection probe is capable of forming a duplex with its complementary sequence through base pairing. In this case, the reporter group (such as a fluorophore) and the quencher group on the detection probe are separated from each other, and the quencher group cannot absorb the signal (e.g., fluorescent signal) from the reporter group, and at this moment, the strongest signal (e.g. fluorescent signal) can be detected. As the temperature increases, the two strands of the duplex begin to dissociate (i.e., the detection probe gradually dissociates from its complementary sequence), and the dissociated detection probe is present in a single-stranded free coil state. In this case, the reporter group (e.g., fluorophore) and the quencher group on the dissociated detection probe are in close proximity to each other, whereby the signal (e.g., fluorescent signal) emitted by the reporter group (e.g., fluorophore) is absorbed by the quencher group. Therefore, as the temperature increases, the detected signal (e.g., the fluorescent signal) gradually becomes weaker. When the two strands of the duplex are completely dissociated, all detection probes are in the single-stranded free coil state. In this case, all the signal (e.g., fluorescent signal) emitted by the reporter group (e.g., fluorophore) on the detection probe is absorbed by the quencher group. Therefore, the signal (e.g., fluorescent signal) emitted by the reporter group (e.g., fluorophore) is essentially undetectable. Therefore, by detecting the signal (e.g., fluorescent signal) emitted by the duplex containing the detection probe during the heating or cooling process, the hybridization and dissociation process of the detection probe and its complementary sequence can be observed, and a curve is formed when the signal intensity changes with temperature. Further, by derivation analysis of the obtained curve, a curve with the change rate of signal intensity as the ordinate and the temperature as the abscissa (that is, a melting curve of the duplex) can be obtained. The peak in the melting curve is the melting peak, and the corresponding temperature is the melting point ($T_m$) of the duplex. In general, the higher the matching degree between the detection probe and the complementary sequence (e.g., fewer mismatched bases and more paired bases), the higher the $T_m$ of the duplex. Therefore, by detecting the $T_m$ of the duplex, the presence and identity of the sequence complementary to the detection probe in the duplex can be determined. As used herein, the terms "melting peak", "melting point" and "$T_m$" have the same meaning and are used interchangeably.

Amplification Method

In one aspect, the present invention provides a method for amplifying one or more target nucleic acids in a sample, comprising, (1) providing a sample containing one or more target nucleic acids; and, providing a first universal primer and a second universal primer, and, for each target nucleic acid to be amplified, providing a target-specific primer pair; wherein, the first universal primer comprises a first universal sequence;

the second universal primer comprises a second universal sequence, and the second universal sequence comprises the first universal sequence and additionally comprises at least one nucleotide at the 3' end of the first universal sequence;

the target-specific primer pair is capable of amplifying the target nucleic acid, and comprises a forward primer and a reverse primer, wherein the forward primer comprises the first universal sequence and a forward nucleotide sequence specific to the target nucleic acid, and the forward nucleotide sequence is located at the 3' end of the first universal sequence; the reverse primer comprises the second universal sequence and a reverse nucleotide sequence specific to the target nucleic acid, and the reverse nucleotide sequence is located at the 3' end of the second universal sequence; and the second universal sequence cannot be completely complementary to the complementary sequence of the forward primer;

(2) amplifying the target nucleic acids in the sample through a PCR reaction using the first universal primer, the second universal primer and the target-specific primer pair under a condition that allows nucleic acid amplification.

In the method of the present invention, the forward primer and the reverse primer respectively comprise a forward nucleotide sequence and a reverse nucleotide sequence specific to the target nucleic acid, whereby, during the PCR reaction, the target-specific primer pair (forward primer and reverse primer) will anneal to the target nucleic acid and initiate PCR amplification, resulting in an initial amplification product comprising two nucleic acid strands (nucleic acid strand A and nucleic acid strand B) respectively complementary to the forward primer and the reverse primer. Further, since both the forward primer and the first universal primer comprise the first universal sequence, the nucleic acid strand A that is complementary to the forward primer can also be complementary to the first universal primer. Similarly, the nucleic acid strand B that is complementary to the reverse primer can also be complementary to the second universal primer.

Therefore, as the PCR reaction proceeds, the first universal primer and the second universal primer will anneal to the nucleic acid strand A and nucleic acid strand B of the initial amplification product, respectively, and further initiate PCR amplification. In this process, since the reverse primer/second universal primer comprises the first universal sequence, the first universal primer can not only anneal to the nucleic acid strand A (nucleic acid strand complementary to the forward primer/first universal primer) and synthesize its complementary strand, and can also anneal to the nucleic acid strand B (nucleic acid strand complementary to the reverse primer/second universal primer) and synthesize its complementary strand. That is, the first universal primer can simultaneously amplify the nucleic acid strand A and nucleic acid strand B of the initial amplification product. At the same time, the second universal primer comprises an additional nucleotide at the 3' end of the first universal sequence, therefore, although the second universal primer may also anneal to the nucleic acid strand A (nucleic acid strand complementary to the forward primer/first universal primer, which has a sequence complementary to the forward primer), it is not matched at the 3' end to the nucleic acid strand A (i.e., not completely complementary at the 3' end). Therefore, during the process of amplification, the second universal primer will preferentially anneal to the nucleic acid strand B (nucleic acid strand complementary to the reverse primer/second universal primer) and synthesize its complementary strand, while will substantially be unable to extend and synthesize the complementary strand of the nucleic acid strand A (nucleic acid strand complementary to the first forward primer/first universal primer).

Therefore, as the PCR amplification proceeds, the synthesis efficiency of the complementary strand (nucleic acid strand B) of nucleic acid strand A will be significantly lower than that of the complementary strand (nucleic acid strand A) of nucleic acid strand B, resulting in that the complementary strand (nucleic acid strand A) of nucleic acid strand B is synthesized and amplified in bulk, while the synthesis and amplification of the complementary strand (nucleic acid strand B) of nucleic acid strand A is inhibited, so that a large amount of single-stranded product (nucleic acid strand A, which contains the sequence complementary to the forward primer/first universal primer and the sequence of the reverse primer/second universal primer) is generated, thereby realizing the asymmetric amplification of the target nucleic acid. Therefore, in certain preferred embodiments, the method of the present invention is capable of carrying out the asymmetric amplification of one or more target nucleic acids in the sample.

In addition, since both the forward primer and reverse primer comprise the first universal sequence, during the PCR reaction, a primer-dimer formed due to the non-specific amplification of the forward primer and reverse primer will generate after denaturation a single-stranded nucleic acid with 5' end and 3' end comprising reverse sequences that are complementary to each other, and the single-stranded nucleic acid is prone to self-annealing in the annealing stage, thereby forming a stable pan-handle structure, preventing the first universal primer and the second universal primer from annealing and extending the single-stranded nucleic acid, thereby inhibiting the further amplification of the primer-dimer. Therefore, in the method of the present invention, the non-specific amplification of the primer-dimer can be effectively suppressed. Therefore, the method of the present invention is particularly suitable to perform multiplex amplification. For example, in the method of the present invention, the first universal primer and the second universal primer can be used in combination with one or more target-specific primer pairs to achieve multiplex amplification of one or more target nucleic acids.

Thus, in certain preferred embodiments, the method of the present invention is capable of simultaneously amplifying 1-5, 5-10, 10-15, 15-20, 20-50 or more target nucleic acids, for example at least 2, at least 3, at least 4, at least 5, at least 8, at least 10, at least 12, at least 15, at least 18, at least 20, at least 25, at least 30, at least 40, at least 50, or more target nucleic acids. In certain preferred embodiments, the method of the present invention is capable of amplifying 1-5, 5-10, 10-15, 15-20, 20-50 or more target nucleic acids simultaneously and asymmetrically. In such embodiments, accordingly, one target-specific primer pair is provided in step (1) for each target nucleic acid to be amplified. Therefore, in such embodiments, in step (1), there is provided with 1-5, 5-10, 10-15, 15-20, 20-50 or more target-specific primer pairs, for example at least 2, at least 3, at least 4, at least 5, at least 8, at least 10, at least 12, at least 15, at least 18, at least 20, at least 25, at least 30, at least 40, at least 50, or more target-specific primer pairs.

It is easy to understand that for different target nucleic acids, different forward primers and reverse primers can be used. However, when there is sequence similarity between different target nucleic acids, different target-specific primer pairs may have the same forward primer or reverse primer.

In order to facilitate the multiplex asymmetric amplification and effectively suppress the non-specific amplification of primer-dimer, in some preferred embodiments, the working concentrations of the first universal primer and the second universal primer are higher than the working concentrations of the forward primer and reverse primer. In certain preferred embodiments, the working concentrations of the first universal primer and the second universal primer are at least 1 times, at least 2 times, at least 3 times, at least 4 times, at least 5 times, at least 8 times, at least 10 times, at least 12 times, at least 15 times, at least 18 times, at least 20 times, at least 25 times, at least 30 times, at least 40 times, at least 50 times or more times higher than the working concentrations of the forward primer and reverse primer. In certain preferred embodiments, the working concentrations of the first universal primer and the second universal primer are 1-5 times, 5-10 times, 10-15 times, 15-20 times, 20-50 times or more times higher than the working concentrations of the forward primer and reverse primer.

In the method of the present invention, the working concentrations of the first universal primer and the second universal primer may be the same or different. In certain preferred embodiments, the working concentrations of the first universal primer and the second universal primer are the same. In certain preferred embodiments, the working concentrations of the first universal primer and the second universal primer are different. As discussed in detail above, in the method of the present invention, the asymmetric amplification is achieved by utilizing the differences in the matching of nucleic acid strands A and B to the first and second universal primers. Therefore, the concentration of the first universal primer relative to the second universal primer may vary. In certain preferred embodiments, the working concentrations of the first universal primer and the second universal primer are the same. In certain preferred embodiments, the working concentration of the first universal primer is higher than that of the second universal primer. In certain preferred embodiments, the working concentration of the first universal primer is lower than that of the second universal primer. As discussed in detail above, the method of the present invention can be used to achieve the asymmetric amplification of target nucleic acids. In some cases, higher amplification asymmetry may be advantageous. Therefore, in some preferred embodiments, the ratio of the first universal primer to the second universal primer can also be adjusted so that the working concentration of the first universal primer is lower than that of the second universal primer, thereby further enhancing the asymmetry of amplification, and better enriching the single-stranded product.

In the method of the present invention, the working concentrations of the forward primer and the reverse primer may be the same or different. In certain preferred embodiments, the working concentrations of the forward primer and the reverse primer are the same. In certain preferred embodiments, the working concentrations of the forward primer and the reverse primer are different. In certain preferred embodiments, the working concentration of the forward primer is lower than the working concentration of the reverse primer. In certain preferred embodiments, the working concentration of the forward primer is higher than the working concentration of the reverse primer.

In certain preferred embodiments, the first universal primer consists of a first universal sequence. In certain preferred embodiments, the first universal primer further comprises an additional sequence located at the 5' end of the first universal sequence. In certain preferred embodiments, the additional sequence comprises one or more nucleotides, such as 1-5, 5-10, 10-15, 15-20 or more nucleotides, for example 1, 2, 3, 4, 5, 6, 7, 8, 9 or 10 nucleotides. In the present application, the first universal primer is used for PCR amplification, so preferably, the first universal sequence is located in or constitutes the 3' portion of the first universal primer.

In the embodiments of the present application, the first universal primer may be of any length as long as it can perform PCR reaction. For example, the first universal primer may have a length of 5-50 nt, such as 5-15 nt, 15-20 nt, 20-30 nt, 30-40 nt, or 40-50 nt.

In certain embodiments of the present application, the first universal primer (or any component thereof) may comprise or consist of a naturally occurring nucleotide (e.g., deoxyribonucleotide or ribonucleotide), a modified nucleotide, a non-natural nucleotide, or any combination thereof. In certain preferred embodiments, the first universal primer (or any component thereof) comprises or consists of a natural nucleotide (e.g., deoxyribonucleotide or ribonucleotide). In certain preferred embodiments, the first universal primer (or any component thereof) comprises a modified nucleotide, for example a modified deoxyribonucleotide or ribonucleotide, such as 5-methylcytosine or 5-hydroxymethylcytosine. In certain preferred embodiments, the first universal primer (or any component thereof) comprises a non-natural nucleotide such as deoxyhypoxanthine, inosine, 1-(2'-deoxy-β-D-ribofuranosyl)-3-nitropyrrole, 5-nitroindole or locked nucleic acid (LNA).

In certain preferred embodiments, the second universal primer consists of a second universal sequence. In certain preferred embodiments, the second universal primer further comprises an additional sequence located at the 5' end of the second universal sequence. In certain preferred embodiments, the additional sequence comprises one or more nucleotides, for example 1-5, 5-10, 10-15, 15-20 or more nucleotides, such as 1, 2, 3, 4, 5, 6, 7, 8, 9 or 10 nucleotides. In the present application, the second universal primer is used for PCR amplification, so preferably, the second universal sequence is located in or constitutes the 3' portion of the second universal primer.

In certain preferred embodiments, the second universal sequence comprises the first universal sequence and additionally comprises at least one nucleotide, for example, 1-5, 5-10, 10-15, 15-20 or more nucleotides, such as 1, 2, 3, 4, 5, 6, 7, 8, 9 or 10 nucleotides, at the 3' end of the first universal sequence.

In embodiments of the present application, the second universal primer may be of any length as long as it is capable of performing a PCR reaction and satisfies the conditions as defined above. For example, the second universal primer may have a length of 8-50 nt, such as 8-15 nt, 15-20 nt, 20-30 nt, 30-40 nt, or 40-50 nt. In embodiments of the present application, the length of the second universal sequence is greater than the length of the first universal sequence.

In certain embodiments of the present application, the second universal primer (or any component thereof) may comprise or consist of a naturally occurring nucleotide (e.g., deoxyribonucleotide or ribonucleotide), a modified nucleotide, a non-natural nucleotide, or any combination thereof. In certain preferred embodiments, the second universal primer (or any component thereof) comprises or consists of a natural nucleotide (e.g., deoxyribonucleotide or ribonucleotide). In certain preferred embodiments, the second universal primer (or any component thereof) comprises a modified nucleotide, for example, modified deoxyribonucleotide or ribonucleotide, such as 5-methylcytosine or 5-hydroxymethylcytosine. In certain preferred embodiments, the second universal primer (or any component thereof) comprises a non-natural nucleotide such as deoxyhypoxanthine, inosine, 1-(2'-deoxy-β-D-ribofuranosyl)-3-nitropyrrole, 5-nitroindole or locked nucleic acid (LNA).

In certain embodiments of the present application, in step (1), there is provided with at least one target-specific primer pair, for example, at least 2, at least 3, at least 4, at least 5, at least 8, at least 10, at least 12, at least 15, at least 18, at least 20, at least 25, at least 30, at least 40, at least 50, or more target-specific primer pairs. In certain preferred embodiments, in step (1), there is provided with 1-5, 5-10, 10-15, 15-20, 20-50 or more target-specific primer pairs. In certain preferred embodiments, the method is capable of amplifying 1-5, 5-10, 10-15, 15-20, 20-50 or more target nucleic acids simultaneously. In certain preferred embodiments, the method is capable of amplifying 1-5, 5-10, 10-15, 15-20, 20-50 or more target nucleic acids simultaneously and asymmetrically.

For example, in certain preferred embodiments, the method of the present invention can be used to amplify 2 target nucleic acids in a sample, wherein in step (1), there is provided with a first universal primer, a second universal primer, a first target-specific primer pair, and a second target-specific primer pair; wherein the first universal primer and the second universal primer are as defined above, and the first target-specific primer pair comprises a first forward primer and a first reverse primer capable of amplifying the first target nucleic acid, the second target-specific primer pair comprises a second forward primer and a second reverse primer capable of amplifying the second target nucleic acid; wherein, the first forward primer, the first reverse primer, the second forward primer and the second reverse primer are as defined above. Similarly, in certain preferred embodiments, the method of the present invention can be used to amplify 3 or more target nucleic acids in a sample, wherein in step (1), there is provided a first universal primer, a second universal primer, and 3 or more target-specific primer pairs capable of amplifying the 3 or more target nucleic acids.

In certain preferred embodiments, in the forward primer, the forward nucleotide sequence is linked directly to the 3' end of the first universal sequence. In certain preferred embodiments, in the forward primer, the forward nucleotide sequence is linked to the 3' end of the first universal sequence by a nucleotide linker. In certain preferred embodiments, the forward primer comprises or consists of a first universal sequence and a forward nucleotide sequence from 5' to 3'. In certain preferred embodiments, the forward primer comprises or consists of a first universal sequence, a nucleotide linker and a forward nucleotide sequence from 5' to 3'. In certain preferred embodiments, the nucleotide linker comprises one or more nucleotides, for example, 1-5, 5-10, 10-15, 15-20 or more nucleotides, such as 1, 2, 3, 4, 5, 6, 7, 8, 9 or 10 nucleotides.

In certain preferred embodiments, the forward primer further comprises an additional sequence located at the 5' end of the first universal sequence. Therefore, in certain preferred embodiments, the forward primer comprises or consists of an additional sequence, a first universal sequence and a forward nucleotide sequence from 5' to 3'. In certain preferred embodiments, the forward primer comprises or consists of an additional sequence, a first universal sequence, a nucleotide linker and a forward nucleotide sequence from 5' to 3'. In certain preferred embodiments, the additional sequence comprises one or more nucleotides, for example, 1-5, 5-10, 10-15, 15-20 or more nucleotides, for example 1, 2, 3, 4, 5, 6, 7, 8, 9 or 10 nucleotides.

In the present application, the forward primer is used for PCR amplification of a target nucleic acid, so preferably, the forward nucleotide sequence is located in or constitutes the 3' portion of the forward primer.

In embodiments of the present application, the forward nucleotide sequence is not limited by its length, as long as it can specifically hybridize with the target nucleic acid sequence and amplify the target nucleic acid. For example, the forward nucleotide sequence may have a length of 10-100 nt, such as 10-20 nt, 20-30 nt, 30-40 nt, 40-50 nt, 50-60 nt, 60-70 nt, 70-nt 80 nt, 80-90 nt, 90-100 nt.

In the embodiments of the present application, the forward primer is not limited by its length, as long as it satisfies the conditions as defined above. For example, the forward primer may have a length of 15-150 nt, such as 15-20 nt, 20-30 nt, 30-40 nt, 40-50 nt, 50-60 nt, 60-70 nt, 70-80 nt, 80-90 nt, 90-100 nt, 100-110 nt, 110-120 nt, 120-130 nt, 130-140 nt, 140-150 nt.

In certain embodiments of the present application, the forward primer (or any component thereof) may comprise or consist of a naturally occurring nucleotide (e.g., deoxyribonucleotide or ribonucleotide), a modified nucleotide, a non-natural nucleotide, or any combination thereof. In certain preferred embodiments, the forward primer (or any component thereof) comprises or consists of a natural nucleotide (e.g., deoxyribonucleotide or ribonucleotide). In certain preferred embodiments, the forward primer (or any component thereof) comprises a modified nucleotide, for example a modified deoxyribonucleotide or ribonucleotide, such as 5-methylcytosine or 5-hydroxymethylcytosine. In certain preferred embodiments, the forward primer (or any component thereof) comprises a non-natural nucleotide such as deoxyhypoxanthine, inosine, 1-(2'-deoxy-β-D-ribofuranosyl)-3-nitropyrrole, 5-nitroindole or locked nucleic acid (LNA).

In certain preferred embodiments, in the reverse primer, the reverse nucleotide sequence is linked directly to the 3' end of the second universal sequence. In certain preferred embodiments, in the reverse primer, the reverse nucleotide sequence is linked to the 3' end of the second universal sequence by a nucleotide linker. In certain preferred embodiments, the reverse primer comprises or consists of a second universal sequence and a reverse nucleotide sequence from 5' to 3'. In certain preferred embodiments, the reverse primer comprises or consists of a second universal sequence, a nucleotide linker and a reverse nucleotide sequence from 5' to 3'. In certain preferred embodiments, the nucleotide linker comprises one or more nucleotides, for example, 1-5, 5-10, 10-15, 15-20 or more nucleotides, such as 1, 2, 3, 4, 5, 6, 7, 8, 9 or 10 nucleotides.

In certain preferred embodiments, the reverse primer further comprises an additional sequence located at the 5' end of the second universal sequence. Therefore, in certain preferred embodiments, the reverse primer comprises or consists of an additional sequence, a second universal sequence and a reverse nucleotide sequence from 5' to 3'. In certain preferred embodiments, the reverse primer comprises or consists of an additional sequence, a second universal sequence, a nucleotide linker and a reverse nucleotide sequence from 5' to 3'. In certain preferred embodiments, the additional sequence comprises one or more nucleotides, for example, 1-5, 5-10, 10-15, 15-20 or more nucleotides, for example 1, 2, 3, 4, 5, 6, 7, 8, 9 or 10 nucleotides.

In the present application, the reverse primer is used for PCR amplification of the target nucleic acid, so preferably, the reverse nucleotide sequence is located in or constitutes the 3' portion of the reverse primer.

In the embodiments of the present application, the reverse nucleotide sequence is not limited by its length, as long as it can specifically hybridize to the target nucleic acid sequence and amplify the target nucleic acid. For example, the reverse nucleotide sequence has a length of 10-100 nt, such as 10-20 nt, 20-30 nt, 30-40 nt, 40-50 nt, 50-60 nt, 60-70 nt, 70-80 nt, 80-90 nt, 90-100 nt.

In the embodiments of the present application, the reverse primer is not limited by its length, as long as it satisfies the conditions as defined above. For example, the reverse primer has a length of 15-150 nt, such as 15-20 nt, 20-30 nt, 30-40 nt, 40-50 nt, 50-60 nt, 60-70 nt, 70-80 nt, 80-90 nt, 90-100 nt, 100-110 nt, 110-120 nt, 120-130 nt, 130-140 nt, 140-150 nt.

In certain embodiments of the present application, the reverse primer (or any component thereof) may comprise or consist of a naturally occurring nucleotide (e.g., deoxyribonucleotide or ribonucleotide), a modified nucleotide, a non-natural nucleotide, or any combination thereof. In certain preferred embodiments, the reverse primer (or any component thereof) comprises or consists of a natural nucleotide (e.g., deoxyribonucleotide or ribonucleotide). In certain preferred embodiments, the reverse primer (or any component thereof) comprises a modified nucleotide, for example modified deoxyribonucleotide or ribonucleotide, such as 5-methylcytosine or 5-hydroxymethylcytosine. In certain preferred embodiments, the reverse primer (or any component thereof) comprises a non-natural nucleotide such as deoxyhypoxanthine, inosine, 1-(2'-deoxy-β-D-ribofuranosyl)-3-nitropyrrole, 5-nitroindole or locked nucleic acid (LNA).

In embodiments of the present application, the second universal sequence is not completely complementary to the complementary sequence of the forward primer. In certain preferred embodiments, at least one nucleotide, for example 1-5, 5-10, 10-15, 15-20 or more nucleotides, such as 1, 2, 3, 4, 5, 6, 7, 8, 9 or 10 nucleotides, at the 3' end of the second universal sequence cannot be complementary to the complementary sequence of the forward primer. Therefore, during the PCR reaction, even if the second universal sequence/second universal primer can anneal to the nucleic acid strand (nucleic acid strand A) complementary to the forward primer, it is substantially be unable to extend and synthesize the complementary strand of the nucleic acid strand.

In the method of the present invention, the sample may be any sample comprising a nucleic acid. For example, in certain preferred embodiments, the sample comprises or is DNA (e.g., genomic DNA or cDNA). In certain preferred embodiments, the sample comprises or is RNA (e.g., mRNA). In certain preferred embodiments, the sample comprises or is a mixture of nucleic acids (e.g., a mixture of DNA, a mixture of RNA, or a mixture of DNA and RNA).

In the method of the present invention, the target nucleic acid to be amplified is not limited by its sequence composition or length. For example, the target nucleic acid can be DNA (e.g., genomic DNA or cDNA) or RNA molecule (e.g., mRNA). Furthermore, the target nucleic acid to be amplified may be single-stranded or double-stranded.

When the sample or target nucleic acid is mRNA, preferably, before carrying out the method of the present invention, a reverse transcription reaction is performed to obtain cDNA complementary to the mRNA. A detailed description of reverse transcription reaction can be found, for example, in Joseph Sam-brook, et al., Molecular Cloning, A Laboratory Manual, Cold Spring Harbor Laboratory Press, Cold Spring Harbor, N.Y. (2001).

In the method of the present invention, the sample or target nucleic acid can be obtained from any source, including but not limited to prokaryote, eukaryote (e.g., protozoan, parasite, fungus, yeast, plant, animal including mammal and human), or virus (e.g., Herpes virus, HIV, influenza virus, EB virus, hepatitis virus, poliovirus, etc.), or viroid. The sample or target nucleic acid can also be any form of nucleic acid, such as genomic nucleic acid, artificially isolated or fragmented nucleic acid, synthetic nucleic acid, and the like.

In the method of the present invention, any nucleic acid polymerase, particularly a template-dependent nucleic acid polymerase, can be used to carry out the PCR reaction. In certain preferred embodiments, the nucleic acid polymerase is a DNA polymerase. In certain preferred embodiments, the nucleic acid polymerase is a thermostable DNA polymerase. The thermostable DNA polymerase can be obtained from various bacterial species such as, but not limited to, *Thermus aquaticus* (Taq), *Thermus thermophiles* (Tth), *Thermus filiformis, Thermis flavus, Thermococcus literalis, Thermus antranildanii, Thermus caldophllus, Thermus chliarophilus, Thermus flavus, Thermus igniterrae, Thermus lacteus, Thermus oshimai, Thermus ruber, Thermus rubens, Thermus scotoductus, Thermus silvanus, Thermus thermophilus, Thermotoga maritima, Thermotoga neapolitana, Thermosipho africanus, Thermococcus litoralis, Thermococcus barossi, Thermococcus gorgonarius, Thermoanatoga maritima, Thermococcus gorgonarius, Thermoanatoga maritima Thermosiphoafricanus, Pyrococcus woesei, Pyrococcus horikoshii, Pyrococcus abyssi, Pyrodictium occultum, Aquifexpyrophilus* and *Aquifex aeolieus*. Particularly preferably, the DNA polymerase is a Taq polymerase.

In certain preferred embodiments, the target nucleic acid is amplified in a three-step process. In such embodiments, each round of nucleic acid amplification requires three steps: nucleic acid denaturation at a first temperature, nucleic acid annealing at a second temperature, and nucleic acid extension at a third temperature. In certain preferred embodiments, the target nucleic acid is amplified in a two-step process. In such embodiments, each round of nucleic acid amplification requires two steps: nucleic acid denaturation at a first temperature, and nucleic acid annealing and extension at a second temperature. Temperatures suitable for nucleic acid denaturation, nucleic acid annealing, and nucleic acid extension can be readily determined by those skilled in the art by routine methods (see, for example, Joseph Sambrook, et al., Molecular Cloning, A Laboratory Manual, Cold Spring Harbor Laboratory Press, Cold Spring Harbor, NY (2001)).

In certain preferred embodiments, steps (1) to (2) of the method of the present invention can be carried out by a protocol comprising the following steps (a) to (f):

(a) providing a sample containing one or more target nucleic acids; and, providing a first universal primer and a second universal primer, and, for each target nucleic acid to be amplified, providing a target-specific primer pair; wherein, the first universal primer, the second universal primer and the target-specific primer pair are as defined above;

(b) mixing the sample with the first universal primer, the second universal primer and the target-specific primer pair, and a nucleic acid polymerase (e.g., a template-dependent nucleic acid polymerase; such as a DNA polymerase, particularly a thermostable DNA polymerase);

(c) incubating the product of the previous step under a condition that allows nucleic acid denaturation;

(d) incubating the product of the previous step under a condition that allows nucleic acid annealing or hybridization;

(e) incubating the product of the previous step under a condition that allows nucleic acid extension; and (f) optionally, repeating steps (c) to (e) once or more times.

In such embodiments, in step (c), all nucleic acid molecules in the sample will dissociate to a single-stranded state; then, in step (d), complementary nucleic acid molecules (e.g., the forward primer and the target nucleic acid or the extension product of the reverse primer, the reverse primer and the target nucleic acid or the extension product of the forward primer, the first universal primer and the amplification product containing the complementary sequence of the first universal sequence, the second universal primer and the amplification product containing the complementary sequence of the second universal sequence) will anneal or hybridize together to form a duplex; then, in step (e), a nucleic acid polymerase (especially a template-dependent nucleic acid polymerase) will extend the forward/reverse primers and the first/second universal primers that hybridize to complementary sequences. Therefore, through the cycle of steps (c) to (e), the amplification of the target nucleic acid sequence (in particular, asymmetric amplification as detailed above) can be achieved, thereby completing steps (1) to (2).

The incubation time and temperature of step (c) can be conventionally determined by those skilled in the art. In certain preferred embodiments, in step (c), the product of step (b) is incubated at a temperature of 80-105° C. (e.g., 80-85° C., 85-90° C., 90-95° C., 91° C., 92° C., 93° C., 94° C., 95° C., 96° C., 97° C., 98° C., 99° C., 100° C., 101° C., 102° C., 103° C., 104° C., or 105° C.), thereby allowing the nucleic acid denaturation. In certain preferred embodiments, in step (c), the product of step (b) is incubated for 10 s-5 min, such as 10-20 s, 20-40 s, 40-60 s, 1-2 min, or 2-5 min.

The incubation time and temperature of step (d) can be conventionally determined by those skilled in the art. In certain preferred embodiments, in step (d), the product of step (c) is incubated at a temperature of 35-70° C. (e.g., 35-40° C., 40-45° C., 45-50° C., 50-55° C., 55-60° C., 60-65° C., or 65-70° C.), thereby allowing the nucleic acid annealing or hybridization. In certain preferred embodiments, in step (d), the product of step (c) is incubated for 10 s-5 min, such as 10-20 s, 20-40 s, 40-60 s, 1-2 min, or 2-5 min.

The incubation time and temperature of step (e) can be conventionally determined by those skilled in the art. In certain preferred embodiments, in step (e), the product of step (d) is incubated at a temperature of 35-85° C. (e.g., 35-40° C., 40-45° C., 45-50° C., 50-55° C., 55-60° C., 60-65° C., 65-70° C., 70-75° C., 75-80° C., 80-85° C.), thereby allowing the nucleic acid extension. In certain preferred embodiments, in step (e), the product of step (d) is incubated for 10 s-30 min, such as 10-20 s, 20-40 s, 40-60 s, 1-2 min, 2-5 min, 5-10 min, 10-20 min or 20-30 min.

In certain embodiments, steps (d) and (e) may be performed at different temperatures, that is, the nucleic acid annealing and extension are performed at different temperatures. In certain embodiments, steps (d) and (e) may be performed at the same temperature, that is, the nucleic acid annealing and extension is performed at the same temperature. In this case, steps (d) and (e) can be combined as one step.

In the method of the present invention, steps (c) to (e) may be repeated at least once, such as at least 2 times, at least 5 times, at least 10 times, at least 20 times, at least 30 times, at least 40 times, or at least 50 times. However, it will be readily understood that when steps (c) to (e) are repeated once or more times, the conditions used in steps (c) to (e) of each cycle need not be the same. For example, one condition can be used to perform steps (c) to (e) of the previous part of the cycles (e.g., the first 5, the first 10, the first 20 cycles), followed by using another condition to perform the steps (c) to (e) of the remaining cycles.

The method of the present invention enables multiplex, asymmetric amplification of target nucleic acid to generate a large amount of single-stranded nucleic acid products. Therefore, the method of the present invention is particularly advantageous in certain circumstances. For example, the amplification product of the method of the present invention can be used for sequencing, for gene chip detection, or for melting curve analysis. Therefore, in some preferred embodiments, the method of the present invention further comprises the step of: (3) sequencing the product in step (2). In certain preferred embodiments, the method of the present invention further comprises the step of: (3) using a gene chip to detect the product in step (2). In certain preferred embodiments, the method of the present invention further comprises the step of: (3) performing melting curve analysis on the product in step (2).

Detection Method

In one aspect, the present application provides a method of detecting one or more target nucleic acids in a sample, comprising, (i) amplifying one or more target nucleic acids in the sample using the method of the present invention; (ii) performing melting curve analysis on the product of step (i).

In certain preferred embodiments, the method of the present invention comprises the steps of:

(1) providing a sample containing one or more target nucleic acids; and, providing a first universal primer and a second universal primer, and, for each target nucleic acid to be amplified, providing a target-specific primer pair and a detection probe; wherein, the first universal primer comprises a first universal sequence;

the second universal primer comprises a second universal sequence, and the second universal sequence comprises the first universal sequence and additionally comprises at least one nucleotide at the 3' end of the first universal sequence;

the target-specific primer pair is capable of amplifying the target nucleic acid and comprises a forward primer and a reverse primer, wherein the forward primer comprises the first universal sequence and a forward nucleotide sequence specific to the target nucleic acid, and the forward nucleotide sequence is located at the 3' end of the first universal sequence; the reverse primer comprises the second universal sequence and a reverse nucleotide sequence specific to the target nucleic acid, and the reverse nucleotide sequence is located at the 3' end of the second universal sequence; and the second universal sequence cannot be completely complementary to a complementary sequence of the forward primer;

the detection probe comprises a probe nucleotide sequence specific to the target nucleic acid, and is labeled with a reporter group and a quencher group, wherein the reporter group is capable of emitting a signal, and the quencher group is capable of absorbing or quenching the signal emitted by the reporter group; and the detection probe emits a signal when hybridized to its complementary sequence that is different from the signal emitted when it is not hybridized to its complementary sequence;

(2) amplifying the target nucleic acids in the sample through a PCR reaction using the first universal primer, the second universal primer, and the target-specific primer pair under a condition that allows nucleic acid amplification;

(3) performing melting curve analysis on the product in step (2) using the detection probe; and determining whether the target nucleic acid exists in the sample according to the result of the melting curve analysis.

In certain embodiments of the present invention, the sample, target nucleic acid, first universal primer, second universal primer and/or target-specific primer pair are as defined above.

In certain embodiments of the present invention, in step (2), the sample is mixed with the first universal primer, the second universal primer and the target-specific primer pair, and a nucleic acid polymerase, and subjected to a PCR reaction. Then, after the PCR reaction is completed, the detection probe is added to the product in step (2), and the melting curve analysis is performed.

In certain embodiments of the present invention, in step (2), the sample is mixed with the first universal primer, the second universal primer, the target-specific primer pair and the detection probe, and a nucleic acid polymerase, and subjected to a PCR reaction. Then, after the PCR reaction is completed, the melting curve analysis is performed.

In certain embodiments of the present invention, the detection probe may comprise or consist of a naturally occurring nucleotide (e.g., deoxyribonucleotide or ribonucleotide), a modified nucleotide, a non-natural nucleotide (e.g., peptide nucleic acid (PNA) or locked nucleic acid), or any combination thereof. In certain preferred embodiments, the detection probe comprises or consists of a natural nucleotide (e.g., deoxyribonucleotide or ribonucleotide). In certain preferred embodiments, the detection probe comprises a modified nucleotide, for example a modified deoxyribonucleotide or ribonucleotide, such as 5-methylcytosine or 5-hydroxymethylcytosine. In certain preferred embodiments, the detection probe comprises a non-natural nucleotide such as deoxyhypoxanthine, inosine, 1-(2'-deoxy-β-D-ribofuranosyl)-3-nitropyrrole, 5-nitroindole or locked nucleic acid (LNA).

In the method of the present invention, the detection probe is not limited by its length. For example, the detection probe may have a length of 15-1000 nt, such as 15-20 nt, 20-30 nt, 30-40 nt, 40-50 nt, 50-60 nt, 60-70 nt, 70-80 nt, 80-90 nt, 90-100 nt, 100-200 nt, 200-300 nt, 300-400 nt, 400-500 nt, 500-600 nt, 600-700 nt, 700-800 nt, 800-900 nt, 900-1000 nt.

In certain preferred embodiments, the detection probe has a 3'-OH terminus. In certain preferred embodiments, the 3'-terminus of the detection probe is blocked to inhibit its extension. The 3'-terminus of nucleic acid (e.g., detection probe) can be blocked by various methods. For example, the 3'-terminus of the detection probe can be blocked by modifying the 3'-OH of the last nucleotide of the detection probe. In certain embodiments, the 3'-terminus of the detection probe can be blocked by adding a chemical moiety (e.g., biotin or alkyl) to the 3'-OH of the last nucleotide of the detection probe. In certain embodiments, the 3'-terminus of the detection probe can be blocked by removing the 3'-OH of the last nucleotide of the detection probe, or by replacing the last nucleotide with a dideoxynucleotide.

As described above, the detection probe is labeled with a reporter group and a quencher group, wherein the reporter group is capable of emitting a signal, and the quencher group is capable of absorbing or quenching the signal emitted by the reporter group; and, the detection probe is able to emit a signal when hybridized to its complementary sequence that is different from the signal emitted when it is not hybridized to its complementary sequence.

In certain preferred embodiments, the detection probe is a self-quenched probe. In such embodiments, when the detection probe is not hybridized to other sequences, the quencher group is located at a position capable of absorbing or quenching the signal of the reporter group (e.g., the quencher group is located adjacent to the reporter group), thereby absorbing or quenching the signal emitted by the reporter group. In this case, the detection probe does not emit a signal. Further, when the detection probe is hybridized to its complementary sequence, the quencher group is located in a position that cannot absorb or quench the signal of the reporter group (e.g., the quencher group is located away from the reporter group), so that it cannot absorb or quench the signal emitted by the reporter group. In this case, the detection probe emits a signal.

The design of such self-quenched detection probe is within the capabilities of those skilled in the art. For example, a reporter group can be labeled at the 5' end of the detection probe and a quencher group can be labeled at the 3' end, or a reporter group can be labeled at the 3' end of the detection probe and a quencher group is labeled at the 5' end. Therefore, when the detection probe exists alone, the reporter group and the quencher group are close to and interact with each other, so that the signal emitted by the reporter group is absorbed by the quencher group, so that the detection probe does not emit a signal; and when the detection probe hybridizes to its complementary sequence, the reporter group and the quencher group are separated from each other, so that the signal emitted by the reporter group cannot be absorbed by the quencher group, thereby causing the detection probe to emit a signal.

It should be understood, however, that the reporter group and the quencher group do not have to be labeled at the ends of the detection probe. The reporter group and/or quencher group can also be labeled internally in the detection probe, as long as the detection probe emits a signal when hybridized to its complementary sequence that is different from the signal emitted when it is not hybridized to its complementary sequence. For example, the reporter group can be labeled in the upstream (or downstream) of the detection probe, and the quencher group can be labeled in the downstream (or upstream) of the detection probe, and the two are separated by a sufficient distance (e.g., 10-20 nt, 20-30 nt, 30-40 nt, 40-50 nt, 50-60 nt, 60-70 nt, 70-80 nt, or longer distance). Therefore, when the detection probe exists alone, the reporter group and the quencher group are close to each other due to the free coiling of the probe molecule or the formation of a secondary structure of the probe (e.g., a hairpin structure) and interact, so that the signal emitted by the reporter group is absorbed by the quencher group, so that the detection probe does not emit a signal; and, when the detection probe hybridizes to its complementary sequence, the reporter group and the quencher group are separated from each other by a sufficient distance such that the signal emitted by the reporter group cannot be absorbed by the quencher group, thereby causing the detection probe to emit a signal. In certain preferred embodiments, the reporter group and the quencher group are separated by a distance of 10-80 nt or more, such as 10-20 nt, 20-30 nt, 30-40 nt, 40-50 nt, 50 nt-60 nt, 60-70 nt, 70-80 nt. In certain preferred embodiments, the reporter group and the quencher group are separated by a distance of no more than 80 nt, no more than 70 nt, no more than 60 nt, no more than 50 nt, no more than 40 nt, no more than 30 nt, or no more than 20 nt. In certain preferred embodiments, the reporter group and the quencher group are separated by a distance of at least 5 nt, at least 10 nt, at least 15 nt, or at least 20 nt.

Therefore, the reporter group and the quencher group can be labeled at any suitable position on the detection probe, as long as the detection probe emits a signal when hybridized to its complementary sequence that is different from the signal emitted when it is not hybridized to its complementary sequence. However, in certain preferred embodiments, at least one of the reporter group and the quencher group is located at the terminus (e.g., the 5' or 3' terminus) of the detection probe. In certain preferred embodiments, one of the reporter group and the quencher group is located at or 1-10 nt from the 5' end of the detection probe, and the reporter group and the quencher group are separated by a suitable distance such that the quencher group can absorb or quench the signal emitted by the reporter group before the detection probe hybridize to its complementary sequence. In certain preferred embodiments, one of the reporter group and the quencher group is located at or 1-10 nt from the 3' end of the detection probe, and the reporter group and the quencher group are separated by a suitable distance such that the quencher group can absorb or quench the signal emitted by the reporter group before the detection probe hybridizes to its complementary sequence. In certain preferred embodiments, the reporter group and the quencher group may be separated by a distance as defined above (e.g., a distance of 10-80 nt or longer). In certain preferred embodiments, one of the reporter group and the quencher group is located at the 5' end of the detection probe, and the other is located at the 3' end.

In the method of the present invention, the reporter group and the quencher group can be any suitable group or molecule known in the art, and their particular examples include, but are not limited to Cy2™ (506), YO-PRO™-1 (509), YOYO™-1 (509), Calcein (517), FITC (518), FluorX™ (519), Alexa™ (520), Rhodamine 110 (520), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), Dil (565), BODIPY TMR (568), BODIPY558/568 (568), BODIPY564/570 (570), Cy3™ (570), Alexa™ 546 (570), TRITC (572), Magnesium Orange™ (575), Phycoerythrin R&B (575), Rhodamine Phalloidin (575), Calcium Orange™ (576), PyroninY (580), Rhodamine B (580), TAMRA (582), Rhodamine Red™ (590), Cy3.5™ (596), ROX (608), Calcium Crimson™ (615), Alexa™ 594 (615), Texas Red (615), Nile Red (628), YO-PRO™-3 (631), YOYO™-3 (631), R-phycocyanin (642), C-Phycocyanin (648), TO-PRO™-3 (660), TOTO3 (660), DiD DilC (5) (665), Cy5™ (670), Thiadicarbocyanine (671), Cy5.5 (694), HEX (556), TET (536), Biosearch Blue (447), CAL Fluor Gold 540 (544), CAL Fluor Orange 560 (559), CAL Fluor Red 590 (591), CAL Fluor Red 610 (610), CAL Fluor Red 635 (637), FAM (520), Fluorescein (520), Fluorescein-C3 (520), Pulsar 650 (566), Quasar 570 (667), Quasar 670 (705), and Quasar 705 (610). The numbers in parentheses indicate the maximum emission wavelength which unit is nm.

In addition, various suitable pairings of the reporter group and the quencher group are known in the art, see, for example, Pesce et al., editors, Fluorescence Spectroscopy (Marcel Dekker, New York, 1971); White et al., Fluorescence Analysis: A Practical Approach (Marcel Dekker, New York, 1970); Berlman, Handbook of Fluorescence Spectra of Aromatic Molecules, 2nd Edition (Academic Press, New York, 1971); Griffiths, Color AND Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); Haugland, R P, Handbook of Fluorescent Probes and Research Chemicals, 6th Edition (Molecular Probes, Eugene, Oreg., 1996); U.S. Pat. Nos. 3,996,345 and 4,351,760.

In certain preferred embodiments, the reporter group is a fluorescent group. In such embodiments, the signal emitted by the reporter group is fluorescence, and the quencher group is a molecule or group capable of absorbing/quenching the fluorescence (e.g., another fluorescent molecule that can absorb the fluorescence, or a quencher that can quench the fluorescence). In certain preferred embodiments, the fluorophore includes, but is not limited to, various fluorescent molecules such as ALEX-350, FAM, VIC, TET, CAL Fluor® Gold 540, JOE, HEX, CAL Fluor Orange 560, TAMRA, CAL Fluor Red 590, ROX, CAL Fluor Red 610, TEXAS RED, CAL Fluor Red 635, Quasar 670, CY3, CY5, CY5.5, Quasar 705, etc. In certain preferred embodiments, the quencher group includes, but is not limited to, various quenchers, such as DABCYL, BHQ (e.g., BHQ-1 or BHQ-2), ECLIPSE, and/or TAMRA, and the like.

In the method of the present invention, the detection probe can also be modified, for example, to endow it with a resistance against nuclease activity (e.g., 5' nuclease activity, for example, 5' to 3' exonuclease activity). For example, a modification resistant to nuclease activity can be introduced into the backbone of the detection probe, examples thereof including phosphorothioate ester bond, alkyl phosphotriester bond, aryl phosphotriester bond, alkyl phosphonate ester bond, aryl phosphonate ester bond, hydrogenated phosphate ester bond, alkyl phosphoramidate ester bond, aryl phosphoramidate ester bond, 2'-O-aminopropyl modification, 2'-O-alkyl modification, 2'-O-allyl modification, 2'-O-butyl modification, and 1-(4'-thio-PD-ribofuranosyl) modification.

In the method of the present invention, the detection probe may be linear, or may have a hairpin structure. In certain preferred embodiments, the detection probe is linear. In certain preferred embodiments, the detection probe has a hairpin structure. The hairpin structure can be natural or artificially introduced. In addition, the detection probe with hairpin structure can be constructed using conventional methods in the art. For example, the detection probe can form a hairpin structure by adding two complementary oligonucleotide sequences to the two ends (5' and 3' ends) of the detection probe. In such embodiments, the two complementary oligonucleotide sequences constitute the arms (stems) of the hairpin structure. The arms of the hairpin structure can be of any desired length, for example the arms may have a length of 2-15 nt, such as 3-7 nt, 4-9 nt, 5-10 nt, 6-12 nt.

In certain embodiments, the product in step (2) can be gradually heated up and the signal emitted by the reporter group on the detection probe can be monitored in real time, so as to obtain a curve of the signal intensity of the product of in step (2) that varies with the change of temperature. For example, the product in step (2) can be heated gradually from a temperature of 45° C. or lower (e.g., no more than 45° C., no more than 40° C., no more than 35° C., no more than 30° C., no more than 25° C.) to a temperature of 75° C. or higher (e.g., at least 75° C., at least 80° C., at least 85° C., at least 90° C., at least 95° C.), and the signal emitted by the reporter group on the detection probe is monitored in real time, so as to obtain a curve of the signal intensity of the reporter group that varies with the change of temperature. The rate of heating can be routinely determined by those skilled in the art. For example, the rate of heating can be as follows: the temperature is elevated per step by 0.01-1° C. (e.g., 0.01-0.05° C., 0.05-0.1° C., 0.1-0.5° C., 0.5-1° C., 0.04-0.4° C., such as 0.01° C., 0.02° C., 0.03° C. ° C., 0.04° C., 0.05° C., 0.06° C., 0.07° C., 0.08° C., 0.09° C., 0.1° C., 0.2° C., 0.3° C., 0.4° C., 0.5° C., 0.6° C., 0.7° C., 0.8° C., 0.9° C. or 1.0° C.), and each step is maintained for 0.5-15 s (e.g., 0.5-1 s, 1-2 s, 2-3 s, 3-4 s, 4-5 s, 5-10 s, 10-15 s); or the temperature is elevated per second by 0.01-1° C. (e.g., 0.01-0.05° C., 0.05-0.1° C., 0.1-0.5° C., 0.5-1° C., 0.04-0.4° C., such as 0.01° C., 0.02° C., 0.03° C., 0.04° C., 0.05° C., 0.06° C., 0.07° C., 0.08° C., 0.09° C., 0.1° C., 0.2° C., 0.3° C., 0.4° C., 0.5° C., 0.6° C., 0.7° C., 0.8° C., 0.9° C. or 1.0° C.).

In certain embodiments, the product in step (2) can be gradually cooled and the signal emitted by the reporter group of the detection probe can be monitored in real time, so as to obtain a curve in which the signal intensity of the product in step (2) varies with the change in temperature. For example, the product in step (2) can be gradually cooled from a temperature of 75° C. or higher (e.g., at least 75° C., at least 80° C., at least 85° C., at least 90° C., at least 95° C.) to a temperature of 45° C. or lower (e.g., no more than 45° C., no more than 40° C., no more than 35° C., no more than 30° C., no more than 25° C.), and the signal emitted by the reporter group on the detection probe is monitored, so as to obtain a curve of the signal intensity of the reporter group that varies with the change of temperature. The rate of cooling can be routinely determined by those skilled in the art. For example, the rate of cooling may be as follows: the temperature is reduced per step by 0.01-1° C. (e.g., 0.01-0.05° C., 0.05-0.1° C., 0.1-0.5° C., 0.5-1° C., 0.04-0.4° C., such as 0.01° C., 0.02° C., 0.03° C. ° C., 0.04° C., 0.05° C., 0.06° C., 0.07° C., 0.08° C., 0.09° C., 0.1° C., 0.2° C., 0.3° C., 0.4° C., 0.5° C., 0.6° C., 0.7° C., 0.8° C., 0.9° C. or 1.0° C.), and each step is maintained for 0.5-15 s (e.g. 0.5-1 s, 1-2 s, 2-3 s, 3-4 s, 4-5 s, 5-10 s, 10-15 s); or the temperature is reduced per second by 0.01-1° C. (e.g., 0.01-0.05° C., 0.05-0.1° C., 0.1-0.5° C., 0.5-1° C., 0.04-0.4° C., such as 0.01° C., 0.02° C., 0.03° C., 0.04° C., 0.05° C., 0.06° C., 0.07° C., 0.08° C., 0.09° C., 0.1° C., 0.2° C., 0.3° C., 0.4° C., 0.5° C., 0.6° C., 0.7° C., 0.8° C., 0.9° C. or 1.0° C.).

Subsequently, the obtained curve can be differentiated to obtain a melting curve for the product in step (2). According to the melting peak (melting point) in the melting curve, the presence of the target nucleic acid corresponding to the melting peak (melting point) can be determined.

In the method of the present invention, the detection probes used may each independently use the same or different reporter groups. In certain preferred embodiments, the detection probes used have the same reporter group. In this case, the melting curve analysis can be performed on the product in step (2), and the presence of a certain target nucleic acid can be determined according to the melting peak (melting point) in the melting curve. In certain preferred embodiments, the detection probes used have different reporter groups. In this case, when the product in step (2) is subjected to melting curve analysis, the signal of each reporter group can be monitored in real time, thereby obtaining a plurality of melting curves corresponding to the signal of one reporter group. Subsequently, the presence of a certain target nucleic acid can be determined according to the signal species of the reporter group and the melting peak (melting point) in the melting curve. Therefore, the method of the present invention can achieve simultaneous detection (multiplex detection) of one or more (e.g., 2, 3, 4, 5, 6, 7, 9, 10, 11, 12, 13, 14, 15, 16, 17, 18, 19, 20 or more) target nucleic acid sequences.

Without being bound by theoretical limitations, for the same one reporter group (same melting curve), the resolution or precision of melting curve analysis can reach 0.5° C. or higher. In other words, the melting curve analysis can distinguish two melting peaks in the same melting curve with melting points that differ by only 0.5° C. or less (e.g., 0.1° C., 0.2° C., 0.3° C., 0.4° C., 0.5° C.). Therefore, in certain embodiments of the method of the present invention, the melting point difference between the various duplexes formed by the various target nucleic acids and their detection probes may be at least 0.5° C. using the same reporter group, so that different duplexes (and thus different target nucleic acids) can be distinguished and discerned by melting curve analysis. However, a greater difference in melting point of two duplexes is preferred in some cases for facilitating the distinguishing and discerning. Therefore, in certain embodiments of the method of the present invention, the difference in melting point between two duplexes can be any desired value (e.g., at least 0.5° C., at least 1° C., at least 2° C., at least 3° C., at least 4° C., at least 5° C., at least 8° C., at least 10° C., at least 15° C., or at least 20° C.), as long as the melting point difference can be distinguished and discerned by the melting curve analysis.

In certain preferred embodiments, steps (1) to (3) of the method of the present invention can be carried out by a protocol comprising the following steps (a) to (g):

(a) providing a sample containing one or more target nucleic acids; and, providing a first universal primer and a second universal primer, and, for each target nucleic acid to be amplified, providing a target-specific primer pair and a detection probe; wherein the first universal primer, the second universal primer, the target-specific primer pair and the detection probe are as defined above;

(b) mixing the sample with the first universal primer, the second universal primer, the target-specific primer pair and the detection probe, and a nucleic acid polymerase (e.g., a template-dependent nucleic acid polymerase; e.g., a DNA polymerase, particularly a thermostable DNA polymerase);

(c) incubating the product of the previous step under a condition that allows nucleic acid denaturation;

(d) incubating the product of the previous step under a condition that allows nucleic acid annealing or hybridization;

(e) incubating the product of the previous step under a condition that allows nucleic acid extension;

(f) optionally, repeating steps (c) to (e) once or more times; and (g) performing melting curve analysis on the product of the previous step.

Regarding steps (a) to (g), they have been described in detail above.

Primer Set and Kit

In one aspect, the present invention provides a primer set, which comprises: a first universal primer and a second universal primer, and, one or more target-specific primer pairs; wherein, the first universal primer comprises a first universal sequence;

the second universal primer comprises a second universal sequence, the second universal sequence comprises the first universal sequence and additionally comprises at least one nucleotide at the 3' end of the first universal sequence;

each target-specific primer pair is capable of amplifying a target nucleic acid, and comprises a forward primer and a reverse primer, wherein the forward primer comprises the first universal sequence and a forward nucleotide sequence specific to the target nucleic acid, and the forward nucleotide sequence is located at the 3' end of the first universal sequence; the reverse primer comprises the second universal sequence and a reverse nucleotide sequence specific to the target nucleic acid, and the reverse nucleotide sequence is located at the 3' end of the second universal sequence; and the second universal sequence cannot be completely complementary to the complementary sequence of the forward primer.

In certain preferred embodiments, the primer set comprises 1-5, 5-10, 10-15, 15-20, 20-50 or more target-specific primer pairs, for example, at least 2, at least 3, at least 4, at least 5, at least 8, at least 10, at least 12, at least 15, at least 18, at least 20, at least 25, at least 30, at least 40, at least 50, or more target-specific primer pairs.

It will be readily understood that such primer set can be used to implement the method of the present invention described in detail above. Therefore, the various technical features described in detail above for the first universal primer, the second universal primer, the target-specific primer pair, the target nucleic acid, and the sample can also be applied to the technical solutions involving the primer set of the present application. Therefore, in certain preferred embodiments, the primer set comprises the first universal primer, the second universal primer and/or the target-specific primer pair as defined above.

In certain preferred embodiments, the primer set can be used to amplify one target nucleic acid in a sample, comprising: a first universal primer and a second universal primer, and, a first target-specific primer pair comprising a first forward primer and a first reverse primer; wherein,

- the first universal primer comprises a first universal sequence;
- the second universal primer comprises a second universal sequence, the second universal sequence comprises the first universal sequence and additionally comprises at least one nucleotide (e.g., 1-5, 5-10, 10-15, 15-20 or more nucleotides) at the 3' end of the first universal sequence;
- the first forward primer comprises the first universal sequence and a first forward nucleotide sequence specific to the first target nucleic acid, and the first forward nucleotide sequence is located at the 3' end of the first universal sequence;
- the first reverse primer comprises the second universal sequence and a first reverse nucleotide sequence specific to the first target nucleic acid, and the first reverse nucleotide sequence is located 3' to the second universal sequence; and,
- the first forward primer and the first reverse primer are capable of specifically amplifying the first target nucleic acid; and,
- the second universal sequence cannot be completely complementary to a complementary sequence of the first forward primer.

In certain preferred embodiments, the primer set can be used to amplify two target nucleic acids in a sample, which comprises: a first universal primer and a second universal primer, and a first target-specific primer pair and a second target-specific primer pair; wherein the first universal primer and the second universal primer are as defined above, and the first target-specific primer pair comprises a first forward primer and a first reverse primer capable of amplifying the first target nucleic acid, the second target-specific primer pair comprises a second forward primer and a second reverse primer capable of amplifying the second target nucleic acid; wherein the first forward primer, the first reverse primer, the second forward primer and the second reverse primer are as defined above. Similarly, in certain preferred embodiments, the primer set of the present invention can be used to amplify 3 or more target nucleic acids in a sample, which comprises: a first universal primer, a second universal primer, and 3 or more target-specific primer pairs capable of amplifying the 3 or more target nucleic acids.

In addition, for convenience, the primer set of the present invention can be combined with one or more reagents required for carrying out the method (amplification method or detection method) of the present invention to prepare a kit. It will be readily understood that such kit can be used to implement the method of the present invention described in detail above. Therefore, the various technical features detailed above for the various components are equally applicable to the various components in the kit. Moreover, such kit may also contain other reagents required for carrying out the method of the present invention.

Therefore, in another aspect, the present application provides a kit, which comprises the primer set as described above, and, one or more components selected from the group consisting of: a nucleic acid polymerase, a reagent for nucleic acid amplification, a reagent for sequencing, a reagent for gene chip detection, a reagent for melting curve analysis, or any combination thereof.

In certain preferred embodiments, the nucleic acid polymerase is a template-dependent nucleic acid polymerase, such as a DNA polymerase, particularly a thermostable DNA polymerase. In certain preferred embodiments, the nucleic acid polymerase is as defined above.

The reagent for nucleic acid amplification can be conventionally determined by those skilled in the art, and include, but are not limited to, working buffer for enzyme (e.g., nucleic acid polymerase), dNTPs (labeled or unlabeled), water, solution containing ion (e.g., $Mg^{2+}$), single-strand DNA-binding protein (SSB), or any combination thereof.

The reagent for sequencing can be conventionally determined by those skilled in the art, and include, but are not limited to, working buffer for enzyme (e.g., nucleic acid polymerase), dNTPs (labeled or unlabeled), ddNTPs (labeled or unlabeled), water, solution containing ion (e.g., $Mg^{2+}$), single-strand DNA-binding protein (SSB), ligase, nucleic acid linker, sequencing primer, or any combination thereof.

The reagent for gene chip detection can be conventionally determined by those skilled in the art, and include, but are not limited to, working buffer for enzyme (e.g., nucleic acid polymerase), dNTPs (labeled or unlabeled), water, hybridization buffer, washing buffer, labeling reagent, or any combination thereof.

The reagent for melting curve analysis can be conventionally determined by those skilled in the art, and include, but are not limited to, detection probe. In certain preferred embodiments, the detection probe is a self-quenched probe, for example, a self-quenched fluorescent probe. In certain preferred embodiments, the detection probe is as defined above.

Based on the principles described in detail in the present application, those skilled in the art can modify, replace or combine various technical features of the technical solutions of the present invention without departing from the spirit and scope of the present invention. All such technical solutions and modifications thereof are included within the scope of the claims of the present application or their equivalents.

BENEFICIAL EFFECTS OF THE PRESENT INVENTION

Compared with the prior art, the technical solution of the present invention has the following beneficial effects:

(1) Compared with the conventional HAND system and the amplification method using the conventional HAND system, the technical solution of the present invention can realize simultaneous and asymmetric amplification (multiplex, asymmetric amplification) of multiple target nucleic acids.

(2) Compared with the conventional multiplex and asymmetric PCR amplification methods, the technical solution of the present invention can effectively inhibit the non-specific amplification of primer-dimer, and significantly improve the specificity of amplification and the sensitivity of detection.

Therefore, the present invention develops a new method capable of simultaneously and asymmetrically amplifying multiple target nucleic acids, which can simultaneously achieve effective multiplex PCR amplification and asymmetric PCR amplification, and satisfy the clinical requirements for simultaneously performing the amplification and detection of multiple target nucleic acids.

The embodiments of the present invention will be described in detail below with reference to the drawings and examples, but those skilled in the art will understand that the following drawings and examples are only used to illustrate the present invention, rather than limit the scope of the present invention. Various objects and advantageous aspects of the present invention will become apparent to those skilled in the art from the accompanying drawings and the following detailed description of the preferred embodiments.

BRIEF DESCRIPTION OF THE DRAWINGS

FIG. 1A schematically shows a primer set used in this embodiment, comprising: a first universal primer and a second universal primer, and a first target-specific primer pair comprising a first forward primer and a first reverse primer; wherein,

- the first universal primer comprises a first universal sequence (Tag1);
- the second universal primer comprises a second universal sequence (Tag2), the second universal sequence comprises the first universal sequence and additionally comprises at least one nucleotide (e.g., 1-5, 5-10, 10-15, 15-20 or more nucleotides) at the 3' end of the first universal sequence;
- the first forward primer comprises the first universal sequence and a first forward nucleotide sequence specific to the first target nucleic acid, and the first forward nucleotide sequence is located at the 3' end of the first universal sequence;
- the first reverse primer comprises the second universal sequence and a first reverse nucleotide sequence specific to the first target nucleic acid, and the first reverse nucleotide sequence is located 3' to the second universal sequence; and,
- the first forward primer and the first reverse primer are capable of specifically amplifying the first target nucleic acid; and,
- the second universal sequence is not completely complementary to a complementary sequence of the first forward primer.

Figure 1:
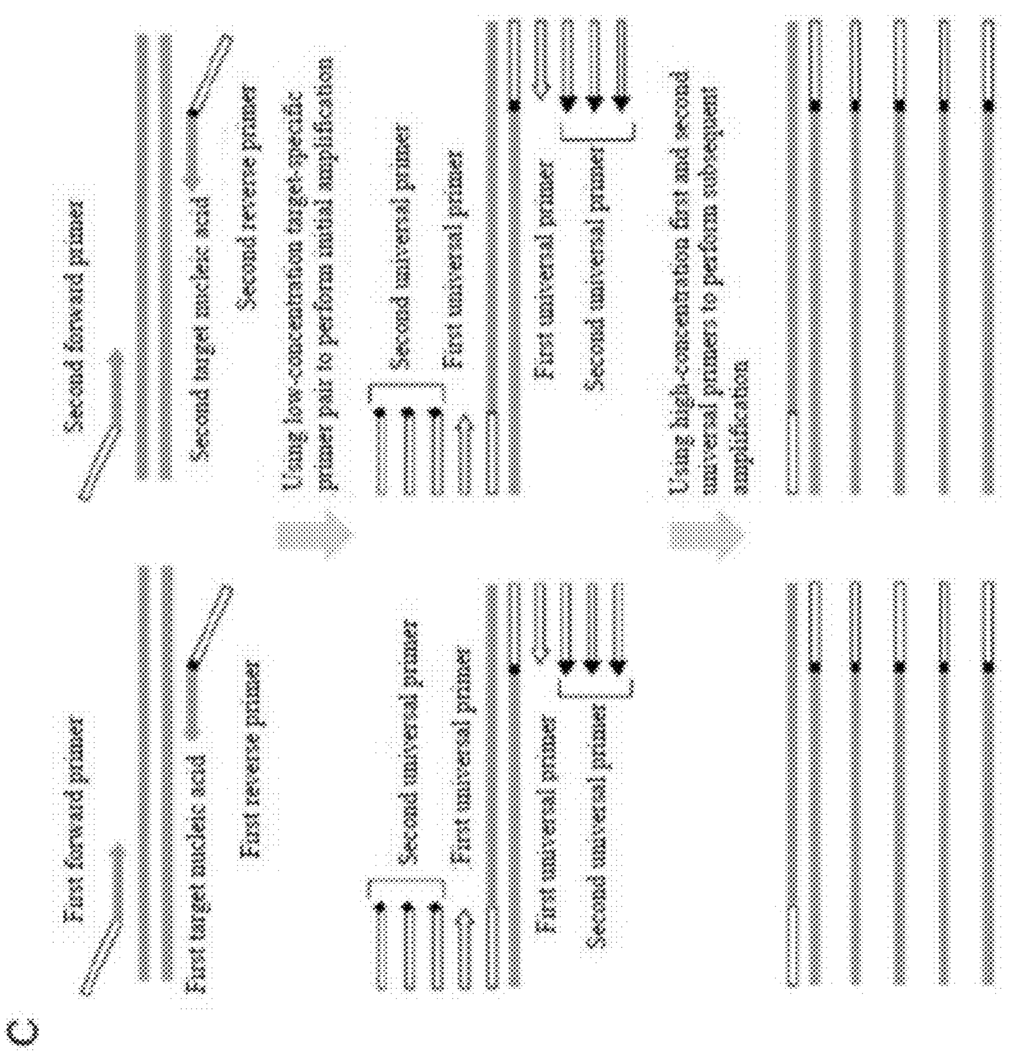
FIG. 1 schematically shows an exemplary embodiment of the method of the present invention to illustrate the basic principle of the method of the present invention.
Figure 1:
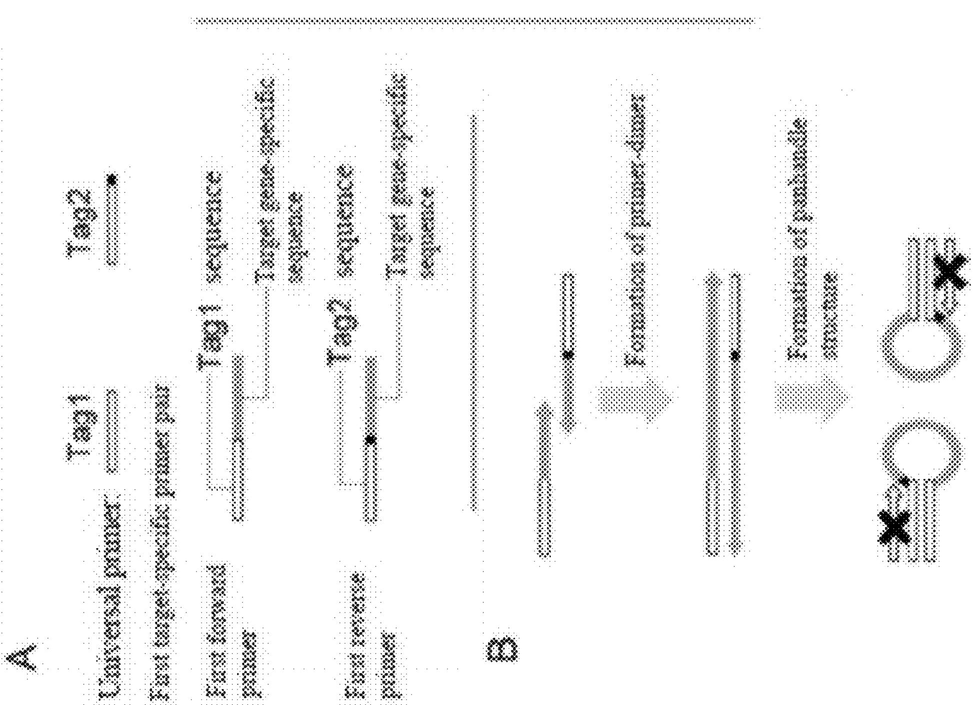

FIG. 1B schematically shows the principle that the non-specific amplification of primer-dimer is suppressed when the primer set of FIG. 1A is used for amplification, wherein the primer-dimer formed due to the non-specific amplification of the first forward primer and the first reverse primer will generate after denaturation a single-stranded nucleic acid whose 5' and 3' ends comprising reverse sequences complementary to each other, and the single-stranded nucleic acid itself will form a stable panhandle structure during the annealing stage, preventing the first universal primer and the second universal primer from annealing and extending the single-stranded nucleic acid, thereby inhibiting the further amplification of the primer-dimer.

FIG. 1C schematically shows the principle of multiplex, asymmetric amplification using the primer set of FIG. 1A. In this embodiment, first, a low concentration of the first target-specific primer pair is used to initiate PCR amplification to generate an initial amplification product, which comprises two nucleic acid strands (nucleic acid strand A and nucleic acid strand B) that are respectively complementary to the first forward primer/first universal primer and the first reverse primer/second universal primer; subsequently, the first universal primer and the second universal primer with a high concentration are used to perform subsequent PCR amplification of the initial amplification product.

Since both the first reverse primer/second universal primer comprise the first universal sequence, the first universal primer can not only anneal to the nucleic acid strand A (nucleic acid strand complementary to the first forward primer/first universal primer) and synthesize its complementary strand, and can also anneal to the nucleic acid strand B (nucleic acid strand complementary to the first reverse primer/second universal primer) and synthesize its complementary strand. That is, the first universal primer can amplify the nucleic acid strand A and the nucleic acid strand B simultaneously.

The second universal primer comprises additional nucleotides at the 3' end of the first universal sequence, so that it is not matched with the nucleic acid strand A (nucleic acid strand complementary to the first forward primer/first universal primer) at the 3' end (i.e., not completely complementary at the 3' end). Therefore, during the amplification process, the second universal primer will preferentially anneal to the nucleic acid strand B (nucleic acid strand complementary to the first reverse primer/second universal primer) and synthesize its complementary strand, while will substantially be unable to extend and synthesize the complementary strand of the nucleic acid strand A (nucleic acid strand complementary to the first forward primer/first universal primer).

Therefore, as the PCR amplification proceeds, the synthesis efficiency of the complementary strand (nucleic acid strand B) of nucleic acid strand A will be significantly lower than that of the complementary strand (nucleic acid strand A) of nucleic acid strand B, resulting in the complementary strand (nucleic acid strand A) of nucleic acid strand B is synthesized and amplified in large quantities, while the synthesis and amplification of the complementary strand (nucleic acid strand B) of nucleic acid strand A is inhibited, resulting a large amount of the target single-stranded product (nucleic acid strand A, which comprises a sequence complementary to the first forward primer/first universal primer, and the sequence of the first reverse primer/second universal primer) to achieve asymmetric amplification. In addition, in order to further enhance the asymmetry of amplification, the ratio of the first universal primer and the second universal primer can also be adjusted, so that the concentration of the first universal primer is lower than that of the second universal primer, so as to better enrich the target single-stranded product.

Further, the first universal primer and the second universal primer as defined above can also be used in combination with at least two or more target-specific primer pairs as defined above, wherein each target-specific primer pair comprises a forward primer and a reverse primer capable of specifically amplifying one target nucleic acid, wherein the forward primer comprises the first universal sequence and a forward nucleotide sequence specific to the target nucleic acid, the reverse primer comprise the second universal sequence and a reverse nucleotide sequence specific to the target nucleic acid, whereby the embodiment (primer set) of the present invention can be used to achieve the multiplex and asymmetric amplification of at least two or more target nucleic acids.

In the exemplary embodiment shown in FIG. 1C, the first universal primer and the second universal primer as defined above are used in combination with two target-specific primer pairs, wherein the first target-specific primer pair comprises a first forward primer and a first reverse primer capable of specifically amplifying the first target nucleic acid, and the first forward primer comprises the first universal sequence and a first forward nucleotide sequence specific to the first target nucleic acid, the first reverse primer comprises the second universal sequence and a first reverse nucleotide sequence specific to the first target nucleic acid; the second target-specific primer pair comprises a second forward primer and a second reverse primer capable of specifically amplifying the second target nucleic acid, and the second forward primer comprises the first universal sequence and a second forward nucleotide sequence specific to the second target nucleic acid, and the second reverse primer comprises the second universal sequence and a second reverse nucleotide sequence specific to the second target nucleic acid. Therefore, the primer set can be used to achieve simultaneous, asymmetric amplification of the first and second target nucleic acids.

Figure 2:
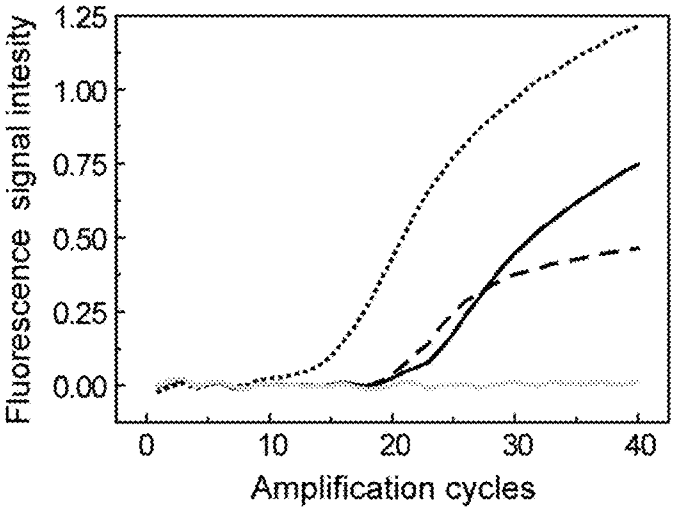

FIG. 2 shows the results of real-time PCR amplification using the HAND system, the conventional asymmetric PCR system and the system of the present invention in Example 1; wherein, the black and gray dashed lines represent amplification curves of using the HAND system to amplify human genomic DNA and the negative control, respectively; the black and gray dotted lines represent amplification curves of using the conventional asymmetric PCR system to amplify human genomic DNA and the negative control, respectively; the black and gray solid lines represent amplification curves of using the system of the present invention to amplify human genomic DNA and the negative control, respectively.

Figure 3:
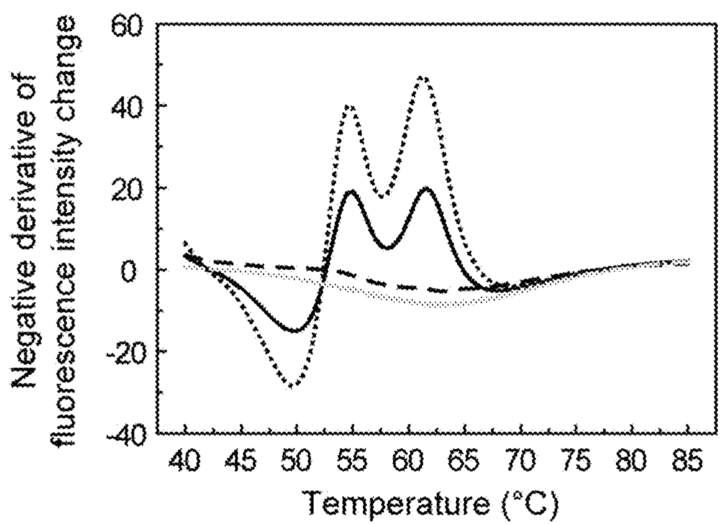

FIG. 3 shows the results of melting curve analysis after amplification using the HAND system, the conventional asymmetric PCR system and the system of the present invention in Example 1; wherein, the black and gray dashed lines represent the results of melting curve analysis after using the HAND system to amplify human genomic DNA and the negative control, respectively; the black and gray dotted lines represent the results of melting curve analysis after using the conventional asymmetric PCR system to amplify human genomic DNA and the negative control, respectively; the black and gray solid lines represent the results of melting curve analysis after using the system of the present invention to amplify human genomic DNA and the negative control, respectively.

Figure 4:
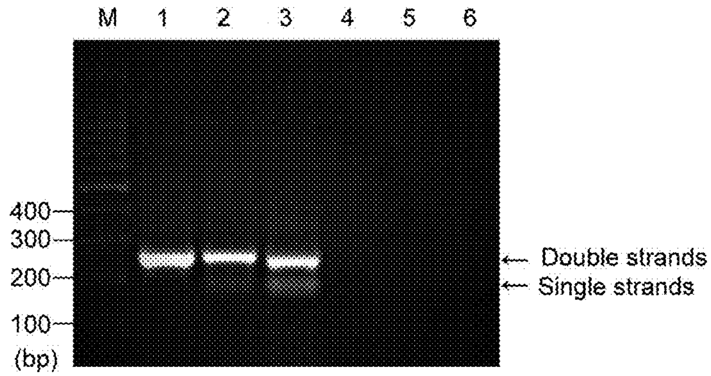

FIG. 4 shows the results of agarose gel electrophoresis of the amplification products obtained by using the HAND system, the conventional asymmetric PCR system and the system of the present invention in Example 1; wherein, lane M represents molecular weight marker; lanes 1 to 3 represent the products of amplifying human genomic DNA by using the HAND system (lane 1), the system of the present invention (lane 2) and the conventional asymmetric PCR system (lane 3), respectively; lanes 4 to 6 represent the products of amplifying the negative control by using the HAND system, the system of the present invention and the conventional asymmetric PCR system, respectively.

Figure 5:
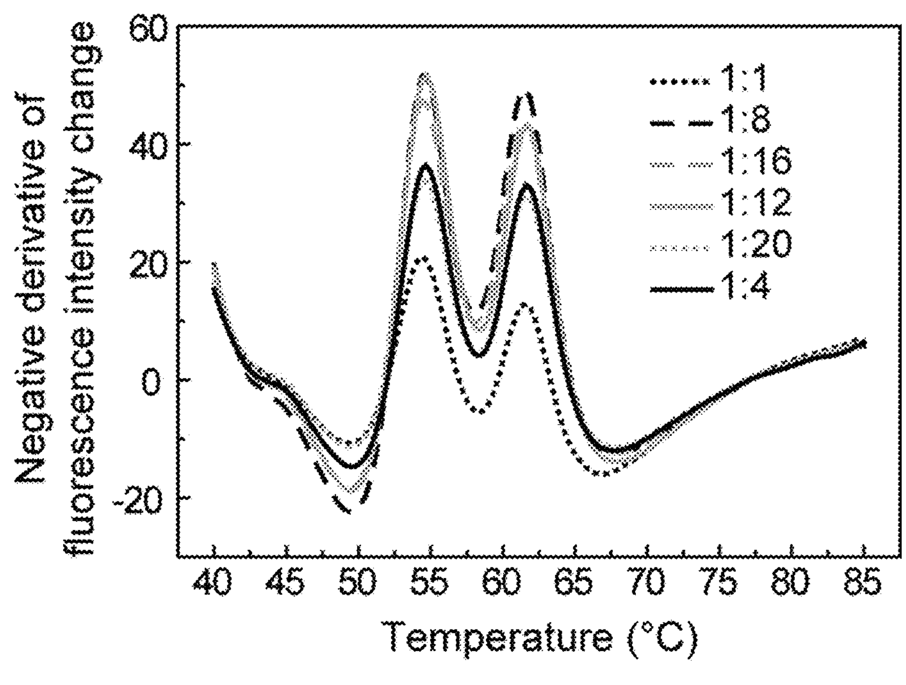

FIG. 5 shows the results of melting curve analysis after amplification using the system of the present invention with different ratios of the first and second universal primers in Example 2.

Figure 6:
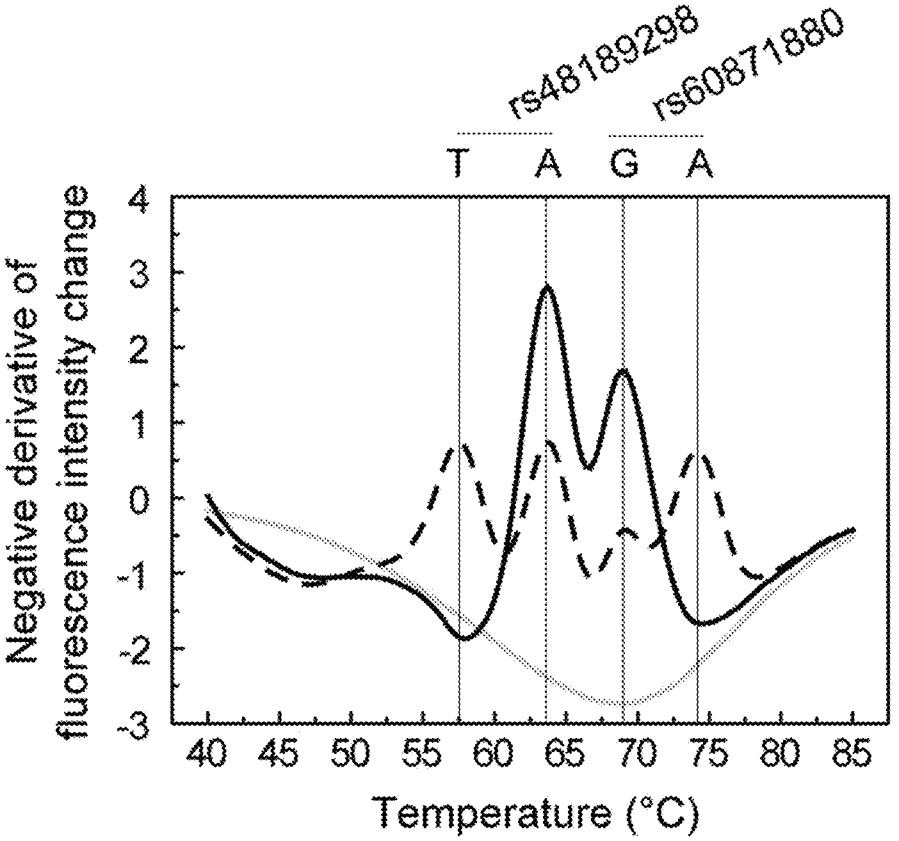

FIG. 6 shows the results of melting curve analysis after amplification using the system of the present invention in Example 3, wherein the black solid line represents the result of melting curve analysis after amplification of Sample 1 using the system of the present invention; the black dashed line represents the result of melting curve analysis after amplification of Sample 2 using the system of the present invention; the gray solid line represents the result of melting curve analysis after amplification of the negative control using the system of the present invention.

Figure 7:
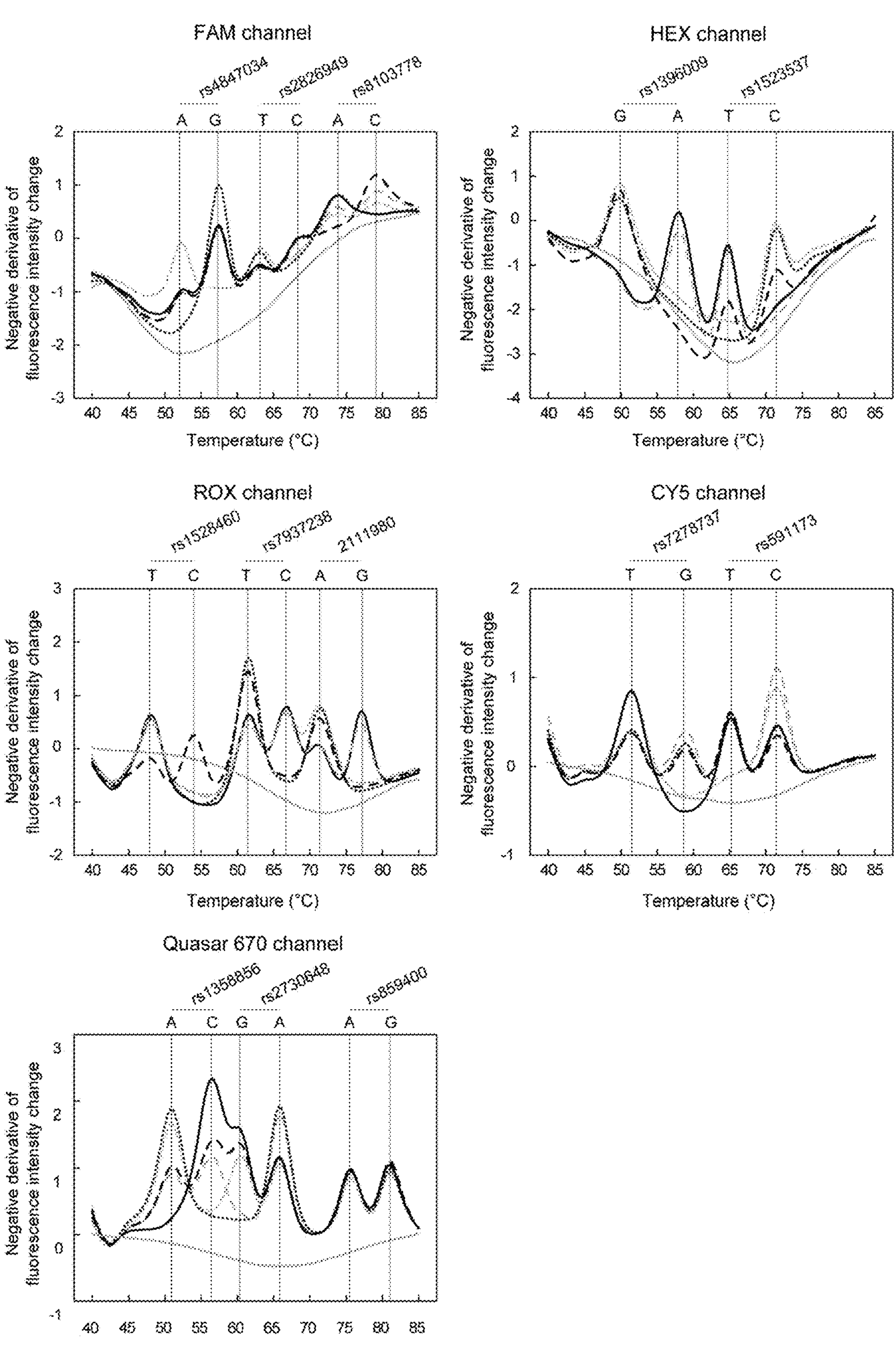

FIG. 7 shows the results of melting curve analysis after amplification using the system of the present invention in Example 4, wherein the black solid line (Sample 3), the black dashed line (Sample 4), the black dotted line (Sample 5), the gray dashed line (Sample 6) and the gray dotted line (Sample 7) respectively represent the result of melting curve analysis after using the system of the present invention to amplify Samples 3 to 7; the gray solid line represents the results of melting curve analysis after using the system of the present invention to amplify the negative control.

Figure 8:
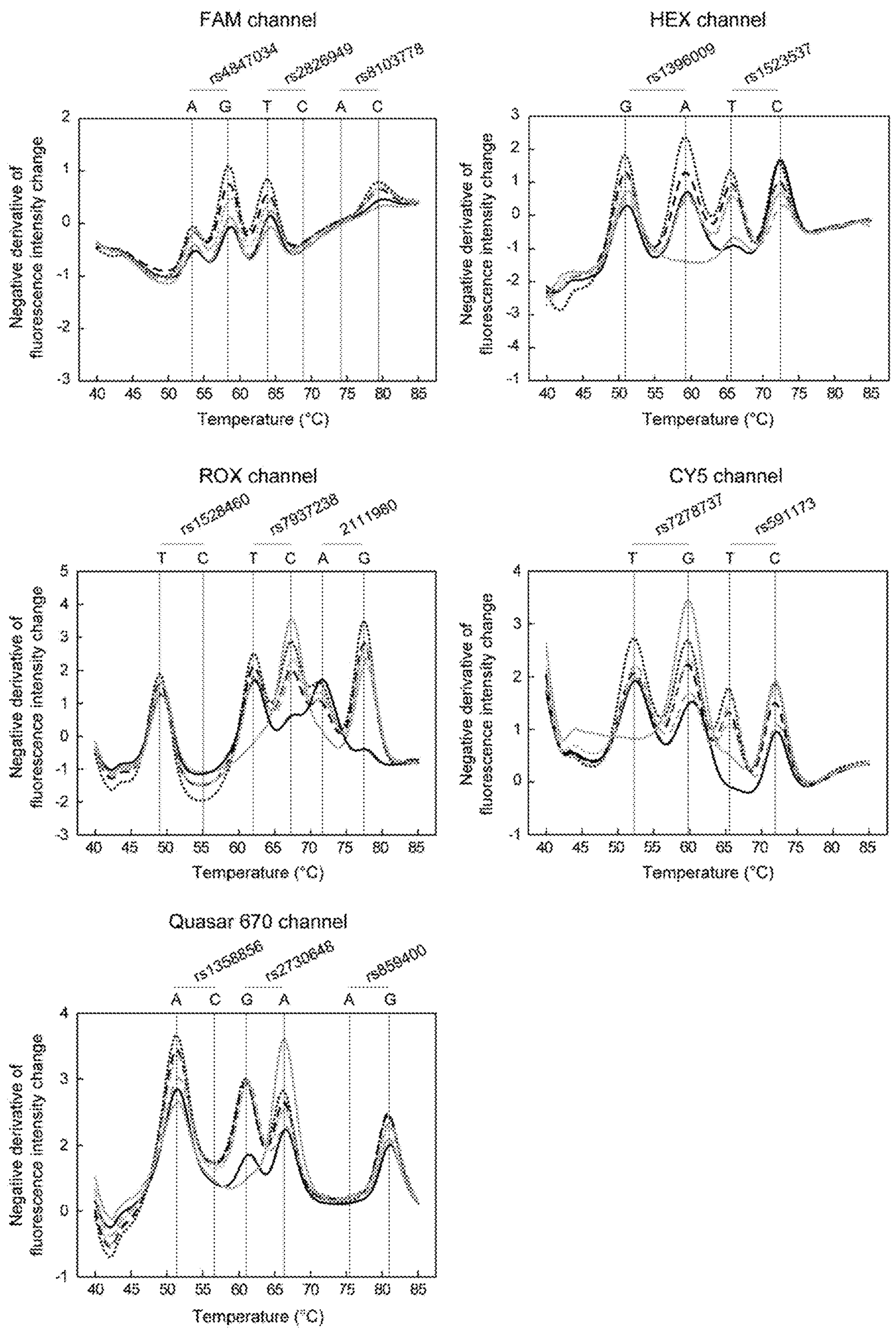

FIG. 8 shows the results of melting curve analysis after amplification using the system of the present invention in Example 5, wherein the black dotted line, the black dashed line, the gray dotted line, the gray dashed line, the black solid line, and the gray solid line represent, respectively, the results of melting curve analysis after amplification of samples with genomic DNA concentrations of 10 ng/μL, 1 ng/μL, 0.1 ng/μL, 0.05 ng/μL, 0.02 ng/μL, or 0.01 ng/μL.

Figure 9:
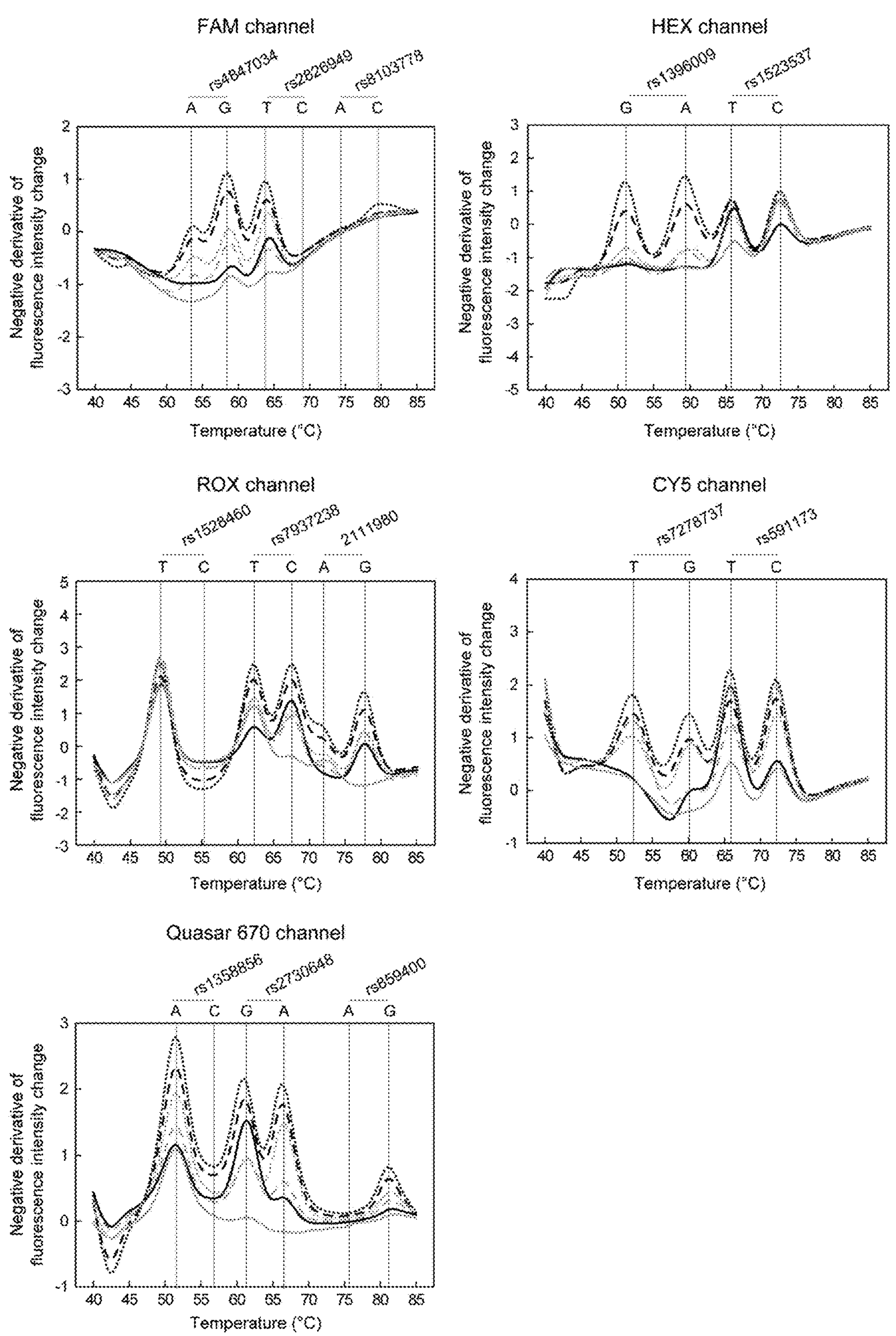

FIG. 9 shows the results of melting curve analysis after amplification using the conventional multiplex asymmetric PCR system in Example 5, wherein the black dotted line, the black dashed line, the gray dotted line, the gray dashed line, the black solid line, and the gray solid line represent, respectively, the results of melting curve analysis after amplification of samples with genomic DNA concentrations of 10 ng/μ, 1 ng/μL, 0.1 ng/μL, 0.05 ng/μL, 0.02 ng/μL, or 0.01 ng/μL.

SPECIFIC MODELS FOR CARRYING OUT THE PRESENT INVENTION

The present invention will now be described with reference to the following examples, which are intended to illustrate, but not limit, the present invention. It should be understood that these examples are only used to illustrate the principles and technical effects of the present invention, but do not represent all possibilities of the present invention. The present invention is not limited to the materials, reaction conditions or parameters mentioned in these examples. Those skilled in the art can implement other technical solutions using other similar materials or reaction conditions according to the principles of the present invention. Such technical solutions do not depart from the basic principles and concepts described in the present invention, and fall into the scope of the present invention.

Example 1

In this example, by using the DNA fragment covering the gene polymorphism site rs8027171 on human chromosome 15 as a target nucleic acid to be amplified, the HAND system, the conventional asymmetric PCR system and the system (primer set) of the present invention were investigated to generate single-stranded nucleic acid product. The sequences of primers and probes used in this example were shown in Table 1. The instrument used in this example was an SLAN 96 real-time fluorescence PCR instrument (Xiamen Zeesan Biotech Co., Ltd., Xiamen).

Briefly, in this example, a 25 μL PCR reaction system was used for PCR amplification and melting curve analysis, and the PCR reaction system comprised: 1×Taq PCR buffer (TaKaRa, Beijing), 5.0 mM $MgCl_2$, 0.2 mM dNTPs, 1 U Taq polymerase (TaKaRa, Beijing), 0.3 μM rs8027171-P probe, 5 μL of human genomic DNA (genotype of rs8027171 was G/A heterozygous) or negative control (water), and primers; in which, (1) the primers used in the HAND system were 0.02 μM rs8027171-F, 0.02 μM rs8027171-R, 0.66 μM Tag 1 primer;

(2) the primers used in the conventional asymmetric PCR systems were 0.06 μM rs8027171-F, 0.6 μM rs8027171-R; and (3) the primers used in the system of the present invention were 0.02 μM rs8027171-F, 0.02 μM rs8027171-R, 0.06 μM Tag 1 primer, and 0.6 μM Tag 2 primer.

The PCR amplification program was as follows: pre-denaturation at 95° C. for 5 min; 10 cycles of (denaturation at 95° C. for 15 s, annealing at 65° C.-56° C. for 15 s (1° C. drop per cycle), extension at 76° C. for 20 s); 50 cycles of (denaturation at 95° C. for 15 s, annealing at 55° C. for 15 s, extension at 76° C. for 20 s); and the fluorescence signal of CY5 channel was collected during the annealing stage. After PCR amplification, the melting curve analysis was carried out, and its program was: denaturation at 95° C. for 1 min; incubation at 37° C. for 3 min; then, the temperature was elevated from 40° C. to 85° C. at a heating rate of 0.04° C./s, and the fluorescence signal of CY5 channel was collected. Finally, each PCR product was analyzed by 2% agarose gel electrophoresis. The experimental results were shown in FIG. 2 to FIG. 4.

TABLE 1

Sequences of primers and probes used in Example 1

| Name | Sequence (5'→3') | SEQ ID No. |
| --- | --- | --- |
| | Primer | |
| rs8027171-F | TCGCAAGCACTCACGTAGAGCAAGTGCAGGTGGAGACA | 1 |
| rs8027171-R | GTCGCAAGCACTCACGTAGAGAGTCGTGGCTAAAGGATAGAAC | 2 |
| Tag 1 primer | TCGCAAGCACTCACGTAGAG | 3 |
| Tag 2 primer | GTCGCAAGCACTCACGTAGAGA | 4 |
| | Fluorescent probe | |
| rs8027171-P | CY5-ATCGGATAGAAAACATGGAGACCGAT-BHQ2 | 5 |

and the negative control, respectively; the black and gray dotted lines represented the results of melting curve analysis after using the conventional asymmetric PCR system to amplify human genomic DNA and the negative control, respectively; the black and gray solid lines represented the results of melting curve analysis after using the system of the present invention to amplify human genomic DNA and the negative control, respectively.

FIG. 4 showed the results of agarose gel electrophoresis of the amplification products obtained by using the HAND system, the conventional asymmetric PCR system and the system of the present invention in Example 1; wherein, lane M represented molecular weight marker; lanes 1 to 3 represented the products of amplifying human genomic DNA by using the HAND system (lane 1), the system of the present invention (lane 2) and the conventional asymmetric PCR system (lane 3), respectively; lanes 4 to 6 represented the products of amplifying the negative control by using the HAND system, the system of the present invention and the conventional asymmetric PCR system, respectively.

The results in FIG. 3 to FIG. 4 showed that when the HAND system was used for amplification, the amplification products were basically a double-stranded nucleic acids and could not produce single-stranded nucleic acid products (FIG. 4, lane 1); accordingly, in the process of melting curve analysis, the probes could not effectively hybridize to the complementary strand of amplification products and could not generate an effective melting peak (FIG. 3, black dashed line). Therefore, when the HAND system was used for amplification, subsequent probe melting curve analysis could not be efficiently performed. However, when the system of the present invention and the conventional asymmetric PCR system were used for amplification, large amounts of single-stranded nucleic acid products were produced (FIG. 4, lanes 2 and 3); therefore, in the process of melting curve analysis, the probe could efficiently hybridize to the amplification products, and generate specific melting peaks (FIG. 3, black solid line and black dotted line). In addition, the results in FIG. 3 to FIG. 4 also showed that none of the negative control systems using water as a template could produce effective melting peaks (FIG. 3, gray dashed line, gray dotted line and gray solid line), this was because that no desired amplification product was generated in the PCR process (FIG. 4, lanes 4 to 6). In addition, as shown in FIG. 3, two melting peaks appeared at the same positions of the black dotted line and the black solid line. This result indicated that the detected sample (target nucleic acid) was heterozygous, which produced two single-stranded nucleic acid products during the amplification process.

The results of this example demonstrated that the system of the present invention could be used to obtain asymmetric FIG. 2 showed the results of real-time PCR amplification using the HAND system, the conventional asymmetric PCR system and the system of the present invention in Example 1; wherein, the black and gray dashed lines represented the amplification curves of using the HAND system to amplify human genomic DNA and the negative control, respectively; the black and gray dotted lines represented the amplification curves of using the conventional asymmetric PCR system to amplify human genomic DNA and the negative control, respectively; the black and gray solid lines represented the amplification curves of using the system of the present invention to amplify human genomic DNA and the negative control, respectively. The results showed that all the three systems could effectively and specifically amplify human genomic DNA, and generate corresponding amplification signals (the black dashed line, the black dotted line, and the black solid line); and the negative controls of each system had no amplification signal (the gray dashed line, the gray dotted line and the gray solid line). In addition, it was noted that the amplification curve (the black dotted line) of the conventional asymmetric PCR system had the smallest Ct value, which is caused by the direct amplification of the target nucleic acid by the high concentration of target-specific primer.

FIG. 3 showed the results of melting curve analysis after amplification using the HAND system, the conventional asymmetric PCR system and the system of the present invention in Example 1; wherein, the black and gray dashed lines represented the results of melting curve analysis after using the HAND system to amplify human genomic DNA amplification of target nucleic acid, and thus could be used in conjunction with probe melting curve analysis.

Example 2

In this example, by using the DNA fragment covering the gene polymorphism site rs8027171 on human chromosome 15 as a target nucleic acid to be amplified, the effect of the ratio of the first and second universal primers on asymmetric amplification was investigated. The sequences of primers and probes used in this example were shown in Table 1. The instrument used in this example was an SLAN 96 real-time fluorescent PCR instrument.

Briefly, in this example, a 25 μL PCR reaction system was used for PCR amplification and melting curve analysis, and the PCR reaction system comprised: 1×Taq PCR buffer, 5.0 mM $MgCl_2$, 0.2 mM dNTPs, 1 U Taq DNA polymerase, 5 μL of human genomic DNA (genotype of rs8027171 was G/A heterozygous), 0.02 μM rs8027171-F, 0.02 μM rs8027171-R, 0.3 μM rs8027171-P probe, 0.06 μM Tag 1 primer, and, Tag 2 primer in the following amounts: 0.06 μM (Tag 1/Tag 2=1/1), 0.24 μM (Tag 1/Tag 2=1/4), 0.48 μM (Tag 1/Tag 2=1/8), 0.72 μM (Tag 1/Tag 2=1/12), 0.96 μM (Tag 1/Tag 2=1/16), or 1.2 μM (Tag 1/Tag 2=1/20).

The PCR amplification program was: pre-denaturation at 95° C. for 5 min; 10 cycles of (denaturation at 95° C. for 15 s, annealing at 65° C.-56° C. for 15 s (1° C. drop for each cycle), extension at 76° C. for 20 s); 50 cycles of (denaturation at 95° C. for 15 s, annealing at 55° C. for 15 s, and extension at 76° C. for 20 s). After the PCR amplification was completed, melting curve analysis was performed, and its program was: denaturation at 95° C. for 1 min; incubation at 37° C. for 3 min; then, the temperature was elevated from 40° C. to 85° C. by a heating rate of 0.04° C./s, and the fluorescence signal of CY5 channel was collected. The melting curve analysis results were shown in FIG. 5.

FIG. 5 showed the results of melting curve analysis after amplification using the system of the present invention with different ratios of the first and second universal primers in Example 2. The results in FIG. 5 showed that under various ratios of Tag 1/Tag 2≤1/1, the system of the present invention could be used to obtain the asymmetric amplification of target nucleic acid, resulting in a single-stranded nucleic acid product, and thus, its amplification product could be used for efficient melting curve analysis. The results in FIG. 5 also showed that different Tag 1/Tag 2 ratios might have an effect on the height of the melting peak. This was because different Tag 1/Tag 2 ratios could affect the amplification efficiency of the PCR reaction, resulting in different yields of single-stranded nucleic acid product. The optimal Tag 1/Tag 2 ratio suitable for the system of the present invention could be adjusted and determined through experiments according to actual conditions.

Example 3

In this example, the typing of gene polymorphism sites rs48189298 and rs60871880 was taken as an example to illustrate that the system of the present invention could realize duplex and asymmetric amplification in a single reaction tube, and could be used for probe melting curve analysis. The sequences of primers and probes used in this example were shown in Table 2. The instrument used in this example was an SLAN 96 real-time fluorescent PCR instrument.

Briefly, in this example, a 25 μL PCR reaction system was used for PCR amplification and melting curve analysis, and the PCR reaction system comprised: 1×Taq PCR buffer, 5.0 mM $MgCl_2$, 0.2 mM dNTPs, 1 U Taq DNA polymerase, 0.04 μM rs48189298-F, 0.04 μM rs48189298-R, 0.4 μM rs48189298-P, 0.06 μM rs60871880-F, 0.06 μM rs60871880-R, 0.4 μM rs60871880-P, 0.2 μM Tag 3 primer, 1.6 μM Tag 2 primer, 5 μL of human genomic DNA or negative control (water). In this example, two samples (Samples 1 and 2) were detected, wherein the genotypes of rs48189298 and rs60871880 sites of Sample 1 were determined to be A/A and G/G by sequencing; the genotypes of rs48189298 and rs60871880 sites of Sample 2 were determined as A/T and G/A by sequencing.

The PCR amplification program was: 95° C. pre-denaturation for 5 min; 10 cycles of (95° C. denaturation for 15 s, 65° C.-56° C. annealing for 15 s (1° C. drop for each cycle), 76° C. extension for 20 s); 50 cycles of (denaturation at 95° C. for 15 s, annealing at 55° C. for 15 s, extension at 76° C. for 20 s). After the PCR amplification, melting curve analysis was carried out, and its program was: denaturation at 95° C. for 1 min; incubation at 37° C. for 3 min; then, the temperature was elevated from 40° C. to 85° C. at a heating rate of 0.04° C./s, and the fluorescence signal of ROX channel was collected. The experimental results were shown in FIG. 6.

TABLE 2

Sequences of primers and probes in Example 3

| Name | Sequence (5'→3') | SEQ ID No. |
|---|---|---|
| | Primer | |
| rs48189298-F | GTCGCAAGCACTCACGTAGAGGAAATTTCAGAATTGTTATGGACCAG | 6 |
| rs48189298-R | GTCGCAAGCACTCACGTAGAGACAGAGGCAGGTCGTCT | 7 |
| rs60871880-F | GTCGCAAGCACTCACGTAGAGCAGGCCCAAATCCATTCTC | 8 |
| rs60871880-R | GTCGCAAGCACTCACGTAGAGATCAAGAGGCACAGCCA | 9 |
| Tag 2 primer | GTCGCAAGCACTCACGTAGAGA | 4 |
| Tag 3 primer | GTCGCAAGCACTCACGTAGAG | 10 |
| | Fluorescent probe | |
| rs48189298-P | ROX-ATGCTCTATGTGTTCAATTTGTTCCGAGCA-BHQ2 | 11 |
| rs60871880-P | ROX-TGTGCTGAAGCTAAGAGCAAAGGGGGCCAGCAC-BHQ2 | 12 |

FIG. 6 showed the results of melting curve analysis after amplification using the system of the present invention in Example 3, wherein the black solid line represented the result of melting curve analysis after Sample 1 was amplified using the system of the present invention; the black dashed line represented the result of melting curve analysis after Sample 2 was amplified using the system of the present invention; the gray solid line represented the result of melting curve analysis after the negative control was amplified using the system of the present invention.

The results in FIG. 6 showed that the genotypes of gene polymorphism sites rs48189298 and rs60871880 in Sample 1 (black solid line) were A/A and G/G, respectively; the genotypes of gene polymorphism sites rs48189298 and rs60871880 in Sample 2 (black dashed line) were A/T and G/A, respectively; the negative control (gray solid line) had no melting peak; the genotype results of each sample were consistent with the results obtained by sequencing. These results showed that the system of the present invention could simultaneously and asymmetrically amplify two target nucleic acids in a single reaction system, and could respectively generate enough single-stranded nucleic acid products for effective and reliable melting curve analysis, thereby realizing the identification of two target nucleic acids (e.g., genotyping of two gene polymorphism sites). Therefore, combined with the melting curve analysis technology, the system of the present invention could simultaneously realize the detection and identification (e.g., genotyping) of two target nucleic acids.

Example 4

In this example, the typing of 13 gene polymorphism sites (i.e., rrs4847034, rs2826949, rs8103778, rs1396009, rs1523537, rs1528460, rs7937238, rs2111980, rs7278737, rs591173, rs1358856, rs2730648 and rs859400) were taken as an example to demonstrate that the system of the present invention could realize 13-plex, asymmetric amplification in a single reaction tube, and could be used for probe melting curve analysis. The sequences of primers and probes used in this example were shown in Table 3. The instrument used in this example was a SLAN 96 real-time fluorescent PCR instrument.

Briefly, in this example, a 25 μL PCR reaction system was used for PCR amplification and melting curve analysis, and the PCR reaction system comprised: 1×Taq PCR buffer, 5.0 mM $MgCl_2$, 0.2 mM dNTPs, 1 U Taq DNA polymerase, 5 μL of human genomic DNA or negative control (water), and, primers and probes. The concentrations of primers and probes used were shown in Table 3. In this example, a total of 5 samples were detected (Samples 3-7; each PCR reaction system was used to detect one of the samples).

The PCR amplification program was: 95° C. pre-denaturation for 5 min; 10 cycles of (denaturation at 95° C. for 15 s, annealing at 65° C.-56° C. for 15 s (1° C. drop for each cycle), extension at 76° C. for 20 s); 50 cycles of (denaturation at 95° C. for 15 s, annealing at 55° C. for 15 s, extension at 76° C. for 20 s). After the PCR amplification, the melting curve analysis was carried out, and its program was: denaturation at 95° C. for 1 min; incubation at 37° C. for 3 min; then, the temperature was elevated from 40° C. to 85° C. at a heating rate of 0.04° C./s, and the fluorescence signals of FAM, HEX, ROX, CY5 and Quasar 705 channels were collected. The experimental results were shown in FIG. 7.

TABLE 3

Sequences of primers and probes used in Example 4

| Name | Sequence (5'→3') | Working concentration (μM) | SEQ ID No. |
|---|---|---|---|
| | Primer | | |
| rs4847034-F | TCGCAAGCACTCACGTAGAGTGGTAATTTGAATTCCTTTGGGT | 0.06 | 13 |
| rs4847034-R | GTCGCAAGCACTCACGTAGAGAGGTGCAGCTATGGCAGA | 0.06 | 14 |
| rs2826949-F | TCGCAAGCACTCACGTAGAGTGTCATCATACTAATGCCTATGTC | 0.06 | 15 |
| rs2826949-R | GTCGCAAGCACTCACGTAGAGAATTAAAGGTTCAAATAAGTAATTACTGT | 0.06 | 16 |
| rs8103778-F | TCGCAAGCACTCACGTAGAGTTGGTCCCTGGCTCTGT | 0.06 | 17 |
| rs8103778-R | GTCGCAAGCACTCACGTAGAGATGAGCTGAGCTTGGGATATG | 0.06 | 18 |
| rs1396009-F | TCGCAAGCACTCACGTAGAGtTGTGAACTTTACTACATAATCTAAGGAA | 0.10 | 19 |
| rs1396009-R | GTCGCAAGCACTCACGTAGAGATTTACTTTTACGTAGTTTTTACTCCA | 0.10 | 20 |
| rs1523537-F | TCGCAAGCACTCACGTAGAGTAAGCCCTTTCATATTTTATGCCT | 0.10 | 21 |
| rs1523537-R | GTCGCAAGCACTCACGTAGAGATTCATAATACAACCTGTCTTTGGA | 0.10 | 22 |
| rs1528460-F | GTCGCAAGCACTCACGTAGAGACTTCCTCCTGGAGATCAATATTT | 0.04 | 23 |
| rs1528460-R | TCGCAAGCACTCACGTAGAGTGATTATGTTGGGATGGGGT | 0.04 | 24 |
| rs7937238-F | GTCGCAAGCACTCACGTAGAGATCAGTCTGATTTAGGTGTGTC | 0.04 | 25 |
| rs7937238-R | TCGCAAGCACTCACGTAGAGTTAGGAGATGTTGTCATGGCA | 0.04 | 26 |
| rs2111980-F | GTCGCAAGCACTCACGTAGAGACGGTCAAAGCATCTTGGC | 0.04 | 27 |
| rs2111980-R | TCGCAAGCACTCACGTAGAGTACAAACTGATCCTATGCAGC | 0.04 | 28 |
| rs7278737-F | TCGCAAGCACTCACGTAGAGCTTTGGTGTACATGTGTTTGGA | 0.06 | 29 |
| rs7278737-R | GTCGCAAGCACTCACGTAGAGAGAGAGAAGGAAATCAACTCTG | 0.06 | 30 |
| rs591173-F | TCGCAAGCACTCACGTAGAGCAAACACATCTCAGTGCTGAC | 0.04 | 31 |
| rs591173-R | GTCGCAAGCACTCACGTAGAGACATAGTGTTTCCATGTGAATGTA | 0.04 | 32 |
| rs1358856-F | GTCGCAAGCACTCACGTAGAGAGCAAATAGAGTTATTTCATCATGGTA | 0.08 | 33 |
| rs1358856-R | TCGCAAGCACTCACGTAGAGGTATTTAATTTTGCTGGCAGTGT | 0.08 | 34 |
| rs2730648-F | TCGCAAGCACTCACGTAGAGTCTTACCTCCAGAGCCTGT | 0.04 | 35 |
| rs2730648-R | GTCGCAAGCACTCACGTAGAGATACCAGAACTATTGAAGGCATC | 0.04 | 36 |
| rs859400-F | GTCGCAAGCACTCACGTAGAGAGCCAACTGCTGCCAAG | 0.04 | 37 |
| rs859400-R | TCGCAAGCACTCACGTAGAGTTGTTCACTCTCCCTCTCTG | 0.04 | 38 |
| Tag 1 primer | TCGCAAGCACTCACGTAGAG | 0.3 | 3 |
| Tag 2 primer | GTCGCAAGCACTCACGTAGAGA | 2.1 | 4 |
| | Fluorescent probe | | |
| rs4847034-P | FAM-TCCGTTTTATTTTTAGTTTGTTTAGAAACGG-BHQ1 | 0.20 | 39 |
| rs2826949-P | FAM-CAGATGGAGTGGTCAAATTTAGTCCTAAGTAACCATCT-BHQ1 | 0.20 | 40 |
| rs8103778-P | FAM-TCGGGACCCCGGCACCACCACCAAGCCATCCCG-BHQ1 | 0.30 | 41 |

TABLE 3-continued

| Sequences of primers and probes used in Example 4 | | | |
|---|---|---|---|
| Name | Sequence (5'→3') | Working concentration (μM) | SEQ ID No. |
| rs1396009-P | HEX-TCGCAGAAGAAAAACATACTTGCG-BHQ1 | 0.30 | 42 |
| rs1523537-P | HEX-CGGCCAAGATCTTGTAGGGACGCTATCGCTGGCC-BHQ1 | 0.30 | 43 |
| rs1528460-P | ROX-TGCCAGTCTTAAATATGTTAAGGCA-BHQ2 | 0.10 | 44 |
| rs7937238-P | ROX-TCCCAGCAGTTCGGTTGACTTTGGGA-BHQ2 | 0.16 | 45 |
| rs2111980-P | ROX-CGCGGAGGCACCAGGCTGGAGCTCGAAGGATCCGC-BHQ2 | 0.20 | 46 |
| rs7278737-P | CY5-CCGAAACACTTCCTCTCTGTCTTCGG-BHQ2 | 0.20 | 47 |
| rs591173-P | CY5-TACGCTGTCCTAAGCACGGGAACAGATACAGCG-BHQ2 | 0.20 | 48 |
| rs1358856-P | Quasar 705-TCTGTGTACATAGCTGTTTGTACAT-BHQ3 | 0.20 | 49 |
| rs2730648-P | Quasar 705-TCCCTTGCTAAGGAACATGAGGATAAGGGA-BHQ3 | 0.16 | 50 |
| rs859400-P | Quasar 705-TGAGTCCTGAGACCACGCTGCGAGCTCCCGGACTC-BHQ3 | 0.30 | 51 |

FIG. 7 showed the results of melting curve analysis after amplification using the system of the present invention in Example 4, wherein, the black solid line (Sample 3), the black dashed line (Sample 4), the black dotted line (Sample 5), the gray dashed line (Sample 6), the gray dotted line (Sample 7) respectively represented the result of melting curve analysis after using the system of the present invention to amplify Samples 3 to 7. The results of melting curve analysis of FIG. 7 were further summarized in Table 4.

TABLE 4

| Typing results of 13 gene polymorphism sites in Samples 3 to 7 | | | | | | |
|---|---|---|---|---|---|---|
| | Sample 3 (black solid line) | Sample 4 (black dashed line) | Sample 5 (black dotted line) | Sample 6 (gray dashed line) | Sample 7 (gray dotted line) | Negative control (gray solid line) |
| rs4847034 | A/G | A/G | G/G | A/G | A/A | — |
| rs2826949 | T/C | T/C | T/T | T/C | T/T | — |
| rs8103778 | A/A | C/C | A/A | A/C | A/C | — |
| rs1396009 | A/A | G/G | G/G | A/A | G/G | — |
| rs1523537 | T/T | T/C | C/C | T/T | C/C | — |
| rs1528460 | T/T | T/C | T/T | T/T | T/T | — |
| rs7937238 | T/C | T/T | T/T | T/C | T/C | — |
| rs2111980 | A/G | A/A | A/A | A/G | A/A | — |
| rs7278737 | T/T | T/G | T/G | T/G | T/T | — |
| rs591173 | T/C | T/C | T/C | C/C | C/C | — |
| rs1358856 | C/C | A/C | A/A | A/C | A/A | — |
| rs2730648 | G/A | G/A | A/A | A/A | G/A | — |
| rs859400 | A/G | A/G | A/G | A/G | A/G | — |

In addition, the genotyping results of 13 gene polymorphism sites in Samples 3 to 7 were also identified by sequencing. The results showed that the genotyping results of each sample obtained by the system of the present invention (FIG. 7 and Table 4) were completely consistent with the results obtained by the sequencing.

These results showed that the system of the present invention could simultaneously asymmetrically amplify 13 target nucleic acids in a sample in a single reaction system, and respectively generate enough single-stranded nucleic acid products for effective and reliable melting curve analysis, and this in turn enabled the identification of multiple target nucleic acids (e.g., genotyping of multiple genetic polymorphism sites). Therefore, combined with the melting curve analysis technology, the system of the present invention could simultaneously realize the detection and identification (e.g., genotyping) of multiple target nucleic acids.

Example 5

In this example, the genotyping of samples containing different concentrations of human genomic DNA was taken as an example to compare the analytical sensitivity of the system of the present invention and the conventional multiplex asymmetric PCR system. The 13 gene polymorphism sites of genomic DNA used in this example were known genotypes, and specifically as follows: rs4847034: A/G; rs2826949: T/T; rs8103778: C/C; rs1396009: A/G; rs1523537: T/C; rs1528460: T/T; rs7937238: T/C; rs2111980: A/G; rs7278737: TIG; rs591173: T/C; rs1358856: A/A; rs2730648: G/A; and rs859400: G/G. The sequences of primers and probes used in this example were shown in Table 3. The instrument used in this example was an SLAN 96 real-time fluorescent PCR instrument.

Briefly, in this example, a 25 μL PCR reaction system was used for PCR amplification and melting curve analysis, and the PCR reaction system comprised: 1×Taq PCR buffer, 7.0 mM $MgCl_2$, 0.2 mM dNTPs, 1 U Taq DNA polymerase, 5 μL of human genomic DNA (at concentrations of 10 ng/μL, 1 ng/μL, 0.1 ng/μL, 0.05 ng/μL, 0.02 ng/μL, or 0.01 ng/4), and primers and probes. The concentrations of primers and probes used were shown in Table 5.

The PCR amplification program was: pre-denaturation at 95° C. for 5 min; 10 cycles of (denaturation at 95° C. for 15 s, annealing at 65° C.-56° C. for 15 s (1° C. drop for each cycle), extension at 76° C. for 20 s); 50 cycles of (denaturation at 95° C. for 15 s, annealing at 55° C. for 15 s, extension at 76° C. for 20 s). After the PCR amplification, the melting curve analysis was carried out, and its program was: denaturation at 95° C. for 1 min; incubation at 37° C. for 3 min; then, the temperature was elevated from 40° C. to 85° C. at a heating rate of 0.04° C./s, and the fluorescent signals of FAM, HEX, ROX, CY5, and Quasar 705 channels were collected. The experimental results were shown in FIG. 8 and FIG. 9.

TABLE 5

| Concentrations of primers and probes used in Example 5 | | | |
|---|---|---|---|
| | Working concentration (μM) | | |
| | The system of the present invention | Conventional multiplex asymmetric PCR system | SEQ ID No. |
| Primer | | | |
| rs4847034-F | 0.06 | 0.06 | 13 |
| rs4847034-R | 0.06 | 0.60 | 14 |
| rs2826949-F | 0.06 | 0.06 | 15 |
| rs2826949-R | 0.06 | 0.60 | 16 |
| rs8103778-F | 0.06 | 0.06 | 17 |
| rs8103778-R | 0.06 | 0.60 | 18 |

TABLE 5-continued

| Concentrations of primers and probes used in Example 5 | | | |
|---|---|---|---|
| | Working concentration (μM) | | |
| | The system of the present invention | Conventional multiplex asymmetric PCR system | SEQ ID No. |
| rs1396009-F | 0.06 | 0.06 | 19 |
| rs1396009-R | 0.06 | 0.60 | 20 |
| rs1523537-F | 0.04 | 0.04 | 21 |
| rs1523537-R | 0.04 | 0.40 | 22 |
| rs1528460-F | 0.04 | 0.40 | 23 |
| rs1528460-R | 0.04 | 0.04 | 24 |
| rs7937238-F | 0.02 | 0.20 | 25 |
| rs7937238-R | 0.02 | 0.02 | 26 |
| rs2111980-F | 0.02 | 0.20 | 27 |
| rs2111980-R | 0.02 | 0.02 | 28 |
| rs7278737-F | 0.03 | 0.03 | 29 |
| rs7278737-R | 0.03 | 0.30 | 30 |
| rs591173-F | 0.02 | 0.02 | 31 |
| rs591173-R | 0.02 | 0.20 | 32 |
| rs1358856-F | 0.03 | 0.30 | 33 |
| rs1358856-R | 0.03 | 0.03 | 34 |
| rs2730648-F | 0.02 | 0.02 | 35 |
| rs2730648-R | 0.02 | 0.20 | 36 |
| rs859400-F | 0.02 | 0.20 | 37 |
| rs859400-R | 0.02 | 0.02 | 38 |
| Tag 1 | 0.3 | 0 | 3 |
| Tag 2 | 2.1 | 0 | 4 |
| Fluorescent probe | | | |
| rs4847034-P | 0.20 | 0.20 | 39 |
| rs2826949-P | 0.20 | 0.20 | 40 |
| rs8103778-P | 0.20 | 0.20 | 41 |
| rs1396009-P | 0.20 | 0.20 | 42 |
| rs1523537-P | 0.20 | 0.20 | 43 |
| rs1528460-P | 0.20 | 0.20 | 44 |
| rs7937238-P | 0.16 | 0.16 | 45 |
| rs2111980-P | 0.20 | 0.20 | 46 |
| rs7278737-P | 0.20 | 0.20 | 47 |
| rs591173-P | 0.20 | 0.20 | 48 |
| rs1358856-P | 0.20 | 0.20 | 49 |
| rs2730648-P | 0.16 | 0.16 | 50 |
| rs859400-P | 0.20 | 0.20 | 51 |

FIG. 8 showed the results of melting curve analysis after amplification using the system of the present invention in Example 5, wherein, the black dotted line, the black dashed line, the gray dotted line, the gray dashed line, the black solid line, and the gray solid line represented the results of melting curve analysis after amplification of samples with DNA concentrations of 10 ng/μL, 1 ng/μL, 0.1 ng/μL, 0.05 ng/μL, 0.01 ng/μL, or 0.005 ng/μL, respectively.

FIG. 9 shows the results of melting curve analysis after amplification using the conventional multiplex asymmetric PCR system in Example 5, wherein, the black dotted line, the black dashed line, the gray dotted line, the gray dashed line, the black solid line, and the gray solid line represented the results of melting curve analysis after amplification of samples with genomic DNA concentrations of 10 ng/μL, 1 ng/μL, 0.1 ng/μL, 0.05 ng/μL, 0.01 ng/μL, or 0.005 ng/μL, respectively.

The results of FIG. 8 showed that even the concentration of human genomic DNA was as low as 0.05 ng/μL (gray dashed line), the system of the present invention could still stably and accurately detect the genotypes of all 13 gene polymorphism sites. In contrast, the results of FIG. 9 showed that the conventional multiplex asymmetric PCR system was able to detect the genotypes of all 13 gene polymorphism sites only when the concentration of human genomic DNA was 10 ng/μL (black dotted line); and when the concentration of human genomic DNA was 1 ng/μL (gray dashed line), the genotypes of some gene polymorphism sites (e.g., sites rs8103778) could no longer be detected and discriminated (no discernable melting peak was generated). This might be because in the conventional multiplex asymmetric PCR reaction system, high concentrations of multiple primers and probes interacted with each other, resulting in the asymmetric amplification of some gene polymorphism sites could not be carried out effectively, and could not generate sufficient amounts of single-stranded products for melting curve analysis.

The above results showed that the detection sensitivity of the system of the present invention was significantly higher than that of the conventional multiplex asymmetric PCR system. This was mainly because the system of the present invention used low-concentration target-specific primers and high-concentration universal primers for amplification, which effectively reduced the interference between primers, reduced non-specific amplification of dimers and so on, and made the amplification of each target nucleic acid in the reaction system to reach equilibrium, thereby improving the detection sensitivity of the entire reaction system.

Although specific embodiments of the present invention have been described in detail, those skilled in the art will appreciate that various modifications and changes can be made to the details in light of all the teachings that have been disclosed, and that these changes are all within the scope of the present invention. The full scope of the present invention is given by the appended claims and any equivalents thereof.

What is claimed is:

1. A method for amplifying one or more target nucleic acids in a sample, comprising:

(1) providing: (i) a sample containing one or more target nucleic acids; (ii) a first universal primer and a second universal primer; and (iii) a target-specific primer pair for each target nucleic acid to be amplified; wherein, the first universal primer comprises a first universal sequence;

the second universal primer comprises a second universal sequence, wherein the second universal sequence comprises the first universal sequence and additionally comprises at least one nucleotide at a 3' end of the first universal sequence;

the target-specific primer pair is capable of amplifying the target nucleic acid and comprises a forward primer and a reverse primer, wherein the forward primer comprises the first universal sequence and a forward nucleotide sequence specific to the target nucleic acid, and the forward nucleotide sequence is located at the 3' end of the first universal sequence; the reverse primer comprises the second universal sequence and a reverse nucleotide sequence specific to the target nucleic acid, and the reverse nucleotide sequence is located at a 3' end of the second universal sequence; and, the second universal sequence is not completely complementary to a complementary sequence of the forward primer; and (2) amplifying the target nucleic acids in the sample through a PCR reaction using the first universal primer, the second universal primer and the target-specific primer pair under a condition that allows nucleic acid amplification.

2. The method according to claim 1, wherein the method has one or more technical features selected from the following:

(1) the method is used to amplify 1-5, 5-10, 10-15, 15-20, 20-50 or more target nucleic acids;

(2) in step (1) of the method, 1-5, 5-10, 10-15, 15-20, 20-50 or more target-specific primer pairs are provided;

(3) in step (2) of the method, the first universal primer and the second universal primer have a working concentration higher than the working concentration of the forward primer and the reverse primer;

(4) in step (2) of the method, the first universal primer and the second universal primer have the same working concentration; or the first universal primer has a working concentration lower than that of the second universal primer;

(5) in step (2) of the method, the forward primer and the reverse primer have the same or different working concentration;

(6) the sample or target nucleic acid comprises mRNA, and before performing step (2) of the method, a reverse transcription reaction is performed on the sample; and (7) in step (2) of the method, a nucleic acid polymerase.

3. The method according to claim 2, wherein the method has one or more technical-features selected from the following:

(1) the first universal primer and the second universal primer have a working concentration 1-5 times, 5-10 times, 10-15 times, 15-20 times, 20-50 times or more times higher than the working concentration of the forward primer and the reverse primer;

(2) the nucleic acid polymerase is a template-dependent nucleic acid polymerase;

(3) the nucleic acid polymerase is a DNA polymerase;

(4) the nucleic acid polymerase is a thermostable DNA polymerase;

(5) the nucleic acid polymerase is obtained from *Thermus aquaticus* (Taq), *Thermus thermophiles* (Tth), *Thermus filiformis, Thermis flavus, Thermococcus literalis, Thermus antranildanii, Thermus caldophllus, Thermus chliarophilus, Thermus flavus, Thermus igniterrae, Thermus lacteus, Thermus oshimai, Thermus ruber, Thermus rubens, Thermus scotoductus, Thermus silvanus, Thermus thermophilus, Thermotoga maritima, Thermotoga neapolitana, Thermosipho africanus, Thermococcus litoralis, Thermococcus barossi, Thermococcus gorgonarius, Thermotoga maritima, Thermotoga neapolitana, Thermosiphoafricanus, Pyrococcus woesei, Pyrococcus horikoshii, Pyrococcus abyssi, Pyrodictium occultum, Aquifexpyrophilus* and *Aquifex aeolieus*; and (6) the nucleic acid polymerase is Taq polymerase.

4. The method according to claim 1, wherein the method has one or more technical features selected from the following:

(1) the first universal primer consists of the first universal sequence, or the first universal primer comprises the first universal sequence and an additional sequence, wherein the additional sequence is located at a 5' end of the first universal sequence;

(2) the first universal sequence is located in a 3' portion of the first universal primer;

(3) the first universal primer has a length of 5-15 nt, 15-20 nt, 20-30 nt, 30-40 nt, or 40-50 nt;

(4) the first universal primer or any component thereof comprises a naturally occurring nucleotide, a modified nucleotide, a non-natural nucleotide, or any combination thereof;

(5) the second universal primer consists of the second universal sequence, or the second universal primer comprises the second universal sequence and an additional sequence, wherein the additional sequence is located at a 5' end of the second universal sequence;

(6) the second universal sequence is located in a 3' portion of the second universal primer;

(7) the second universal primer comprises the first universal sequence and additionally comprises 1-5, 5-10, 10-15, 15-20 or more nucleotides at the 3' end of the first universal sequence;

(8) the second universal primer has a length of 5-15 nt, 15-20 nt, 20-30 nt, 30-40 nt, or 40-50 nt; and (9) the second universal primer or any component thereof comprises a naturally occurring nucleotide, a modified nucleotide, a non-natural nucleotide, or any combination thereof.

5. The method according to claim 1, wherein the method has one or more technical features selected from the following:

(1) in the forward primer, the forward nucleotide sequence is directly linked to the 3' end of the first universal sequence, or the forward nucleotide sequence is linked to the 3' end of the first universal sequence through a nucleotide linker;

(2) the forward primer further comprises an additional sequence, which is located at a 5' end of the first universal sequence;

(3) the forward primer comprises the first universal sequence and the forward nucleotide sequence from 5' to 3'; or, the forward primer comprises the first universal sequence, a nucleotide linker and the forward nucleotide sequence from 5' to 3'; or, the forward primer comprises an additional sequence, the first universal sequence and the forward nucleotide sequence from 5' to 3'; or, the forward primer comprises an additional sequence, the first universal sequence, a nucleotide linker and the forward nucleotide sequence from 5' to 3';

(4) the forward nucleotide sequence is located in a 3' portion of the forward primer;

(5) the forward nucleotide sequence has a length of 10-20 nt, 20-30 nt, 30-40 nt, 40-50 nt, 50-60 nt, 60-70 nt, 70-80 nt, 80-90 nt, or 90-100 nt;

(6) the forward primer has a length of 15-20 nt, 20-30 nt, 30-40 nt, 40-50 nt, 50-60 nt, 60-70 nt, 70-80 nt, 80-90 nt, 90-100 nt, 100-110 nt, 110-120 nt, 120-130 nt, 130-140 nt, or 140-150 nt;

(7) the forward primer or any component thereof comprises a naturally occurring nucleotide, a modified nucleotide, a non-natural nucleotide, or any combination thereof;

(8) in the reverse primer, the reverse nucleotide sequence is directly linked to the 3' end of the second universal sequence, or the reverse nucleotide sequence is linked to the 3' end of the second universal sequence through a nucleotide linker;

(9) the reverse primer further comprises an additional sequence, which is located at a 5' end of the second universal sequence;

(10) the reverse primer comprises the second universal sequence and the reverse nucleotide sequence from 5' to 3'; or, the reverse primer comprises the second universal sequence, a nucleotide linker and the reverse nucleotide sequence from 5' to 3'; or, the reverse primer comprises an additional sequence, the second universal sequence, and the reverse nucleotide sequence from 5' to 3'; or, the reverse primer comprises an additional sequence, the second universal sequence, a nucleotide linker and the reverse nucleotide sequence from 5' to 3';

(11) the reverse nucleotide sequence is located in a 3' portion of the reverse primer;

(12) the reverse nucleotide sequence has a length of 10-20 nt, 20-30 nt, 30-40 nt, 40-50 nt, 50-60 nt, 60-70 nt, 70-80 nt, 80-90 nt, or 90-100 nt;

(13) the reverse primer has a length of 15-20 nt, 20-30 nt, 30-40 nt, 40-50 nt, 50-60 nt, 60-70 nt, 70-80 nt, 80-90 nt, 90-100 nt, 100-110 nt, 110-120 nt, 120-130 nt, 130-140 nt, or 140-150 nt;

(14) the reverse primer or any component thereof comprises a naturally occurring nucleotide, a modified nucleotide, a non-natural nucleotide, or any combination thereof;

(15) at least one nucleotide at the 3' end of the second universal sequence is not complementary to a complementary sequence of the forward primer; and

(16) 1-5, 5-10, 10-15, 15-20 or more nucleotides at the 3' end of the second universal sequence is not complementary to a complementary sequence of the forward primer-.

6. The method according to claim 1, wherein the method has one or more technical features selected from the following:

(1) the sample contains DNA, RNA, or any combination thereof;

(2) the target nucleic acid to be amplified is DNA, RNA, or any combination thereof;

(3) the target nucleic acid to be amplified is single-stranded or double-stranded; and (4) the sample or target nucleic acid is obtained from a prokaryote, a eukaryote, a virus, or a viroid.

7. The method according to claim 6, wherein the method has one or more technical features selected from the following:

(1) said DNA is a genomic DNA or cDNA;

(2) said RNA is a mRNA;

(3) the eukaryote is selected from a protozoan, parasite, fungus, yeast, plant, and animal;

(4) the eukaryote is a mammal;

(5) the eukaryote is a human; and (6) the virus is selected from Herpes virus, HIV, influenza virus, EB virus, hepatitis virus, and polio virus.

8. The method according to claim 1, wherein the steps (1) to (2) of the method are carried out by a protocol comprising the following steps (a) to (f):

(a) providing: (i) the sample containing the one or more target nucleic acids; (ii) the first universal primer and the second universal primer; and (iii) the target-specific primer pair for each target nucleic acid to be amplified;

(b) mixing the sample with the first universal primer, the second universal primer and the target-specific primer pair, and a nucleic acid polymerase;

(c) incubating the product of the previous step under a condition that allows nucleic acid denaturation;

(d) incubating the product of the previous step under a condition that allows nucleic acid annealing or hybridization;

(e) incubating the product of the previous step under a condition that allows nucleic acid extension; and (f) optionally, repeating steps (c) to (e) one or more times.

9. The method according to claim 8, wherein the method has one or more technical features selected from the following:

(1) in step (c), incubating the product of step (b) at a temperature of 80-105° C., thereby allowing the nucleic acid denaturation;

(2) in step (c), incubating the product of step (b) for 10-20 s, 20-40 s, 40-60 s, 1-2 min, or 2-5 min;

(3) in step (d), incubating the product of step (c) at a temperature of 35-40° C., 40-45° C., 45-50° C., 50-55° C., 55-60° C., 60-65° C., or 65-70° C., thereby allowing the nucleic acid annealing or hybridization;

(4) in step (d), incubating the product of step (c) for 10-20 s, 20-40 s, 40-60 s, 1-2 min, or 2-5 min;

(5) in step (e), incubating the product of step (d) at a temperature of 35-40° C., 40-45° C., 45-50° C., 50-55° C., 55-60° C., 60-65° C., 65-70° C., 70-75° C., 75-80° C., 80-85° C., thereby allowing the nucleic acid extension;

(6) in step (e), incubating the product of step (d) for 10-20 s, 20-40 s, 40-60 s, 1-2 min, 2-5 min, 5-10 min, 10-20 min or 20-30 min;

(7) performing steps (d) and (e) at the same or different temperatures; and (8) repeating steps (c) to (e) at least once; optionally, when repeating steps (c) to (e) one or more times, the conditions used in steps (c) to (e) of each cycle are independently the same or different.

10. A method for detecting one or more target nucleic acids in a sample, comprising: (i) using the method according to claim 1 to amplify the one or more target nucleic acids in the sample; and (ii) performing melting curve analysis on the product of step (i).

11. The method according to claim 10, wherein the method comprises the steps of:

(1) providing: (i) a sample containing one or more target nucleic acids; (ii) a first universal primer and a second universal primer; and (iii) a target-specific primer pair and a detection probe for each target nucleic acid to be amplified; wherein, the first universal primer comprises a first universal sequence;

the second universal primer comprises a second universal sequence, wherein the second universal sequence comprises the first universal sequence and additionally comprises at least one nucleotide at a 3' end of the first universal sequence;

the target-specific primer pair is capable of amplifying the target nucleic acid and comprises a forward primer and a reverse primer, wherein the forward primer comprises the first universal sequence and a forward nucleotide sequence specific to the target nucleic acid, and the forward nucleotide sequence is located at the 3' end of the first universal sequence; the reverse primer comprises the second universal sequence and a reverse nucleotide sequence specific to the target nucleic acid, and the reverse nucleotide sequence is located at a 3' end of the second universal sequence; and, the second universal sequence is not completely complementary to a complementary sequence of the forward primer;

the detection probe comprises a probe nucleotide sequence specific to the target nucleic acid, and is labeled with a reporter group and a quencher group, wherein the reporter group is capable of emitting a signal, and the quencher group is capable of absorbing or quenching the signal emitted by the reporter group; and the signal emitted by the detection probe when it hybridizes to its complementary sequence is different from the signal emitted when it is not hybridized to its complementary sequence;

(2) amplifying the target nucleic acids in the sample through a PCR reaction by using the first universal primer, the second universal primer and the target-specific primer pair under a condition that allows nucleic acid amplification; and (3) performing melting curve analysis on the product in step (2) using the detection probe; and determining whether the target nucleic acid exists in the sample according to the result of the melting curve analysis.

12. The method according to claim 11, wherein the method has one or more technical features selected from the following:

(1) the first universal primer consists of the first universal sequence, or the first universal primer comprises the first universal sequence and an additional sequence, wherein the additional sequence is located at a 5' end of the first universal sequence;

(2) the first universal sequence is located in a 3' portion of the first universal primer;

(3) the second universal primer consists of the second universal sequence, or, comprises the second universal sequence and an additional sequence, and the additional sequence is located at a 5' end of the second universal sequence;

(4) the second universal sequence is located in a 3' portion of the second universal primer;

(5) the second universal primer comprises the first universal sequence and additionally comprises 1-5, 5-10, 10-15, 15-20 or more nucleotides at the 3' end of the first universal sequence;

(6) in the forward primer, the forward nucleotide sequence is directly linked to the 3' end of the first universal sequence, or the forward nucleotide sequence is linked to the 3' end of the first universal sequence through a nucleotide linker;

(7) the forward primer further comprises an additional sequence, which is located at the 5' end of the first universal sequence;

(8) the forward primer comprises the first universal sequence and the forward nucleotide sequence from 5' to 3'; or, the forward primer comprises the first universal sequence, a nucleotide linker and the forward nucleotide sequence from 5' to 3'; or, the forward primer comprises an additional sequence, the first universal sequence and the forward nucleotide sequence from 5' to 3'; or, the forward primer comprises an additional sequence, the first universal sequence, a nucleotide linker and the forward nucleotide sequence from 5' to 3';

(9) the forward nucleotide sequence is located in a 3' portion of the forward primer;

(10) in the reverse primer, the reverse nucleotide sequence is directly linked to the 3' end of the second universal sequence, or the reverse nucleotide sequence is linked to the 3' end of the second universal sequence through a nucleotide linker;

(11) the reverse primer further comprises an additional sequence, which is located at the 5' end of the second universal sequence;

(12) the reverse primer comprises the second universal sequence and the reverse nucleotide sequence from 5' to 3'; or, the reverse primer comprises the second universal sequence, a nucleotide linker and the reverse nucleotide sequence from 5' to 3'; or, the reverse primer comprises an additional sequence, the second universal sequence, and the reverse nucleotide sequence from 5' to 3'; or, the reverse primer comprises an additional sequence, the second universal sequence, a nucleotide linker and the reverse nucleotide sequence from 5' to 3';

(13) the reverse nucleotide sequence is located in a 3' portion of the reverse primer; and

(14) at least one nucleotide at the 3' end of the second universal sequence is not complementary to a complementary sequence of the forward primer; and

(15) 1-5, 5-10, 10-15, 15-20 or more nucleotides at the 3' end of the second universal sequence is not complementary to a complementary sequence of the forward primer.

13. The method according to claim 11, wherein the method has one or more technical features selected from the following:

(1) in step (2), the sample is mixed with the first universal primer, the second universal primer, the target-specific primer pair, and the nucleic acid polymerase, and the PCR reaction is performed, and then, after the PCR reaction is completed, the detection probe is added to the product in step (2), and the melting curve analysis is performed; or, in step (2), the sample is mixed with the first universal primer, the second universal primer, the target-specific primer pair and the detection probe, and the nucleic acid polymerase, and the PCR reaction is performed, and then, after the PCR reaction is completed, the melting curve analysis is performed;

(2) the detection probe comprises a naturally occurring nucleotide, a modified nucleotide, a non-natural nucleotide, or any combination thereof;

(3) the detection probe has a length of 15-20 nt, 20-30 nt, 30-40 nt, 40-50 nt, 50-60 nt, 60-70 nt, 70-80 nt, 80-90 nt, 90-100 nt, 100-200 nt, 200-300 nt, 300-400 nt, 400-500 nt, 500-600 nt, 600-700 nt, 700-800 nt, 800-900 nt, or 900-1000 nt;

(4) the detection probe has a 3'-OH terminus; or, a 3'-terminus of the detection probe is blocked;

(5) the detection probe is a self-quenched probe;

(6) the reporter group in the detection probe is a fluorescent group; and the quencher group is a molecule or group capable of absorbing/quenching the fluorescence;

(7) the detection probe has a resistance against nuclease activity;

(8) the detection probe is linear or has a hairpin structure;

(9) each of the detection probes independently has the same or different reporter group;

(10) in step (3), the product in step (2) is gradually heated or cooled and the signal emitted by the reporter group on each detection probe is monitored in real time, so as to obtain a curve of signal intensity of each reporter group that varies with the change of temperature; then, the curve is differentiated to obtain a melting curve of the product in step (2); and

(11) the presence of the target nucleic acid corresponding to the melting peak (melting point) is determined according to the melting peak (melting point) in the melting curve.

14. The method according to claim 13, wherein the method has one or more technical features selected from the following:

(1) the naturally occurring nucleotide is a deoxyribonucleotide or a ribonucleotide;

(2) the non-natural nucleotide is a peptide nucleic acid (PNA) or a locked nucleic acid;

(3) the 3'-terminus of the detection probe is blocked by adding a chemical moiety to the 3'-OH of the last nucleotide of the detection probe, by removing the 3'-OH of the last nucleotide of the detection probe, or by replacing the last nucleotide with a dideoxynucleotide;

(4) the 3'-terminus of the detection probe is blocked by adding a biotin or an alkyl to a 3'-OH of the last nucleotide of the detection probe;

(5) the reporter group and the quencher group are separated by a distance of 10-80 nt or more;

(6) the reporter group is one or more fluorescent molecules;

(7) the detection probe has a resistance against 5' nuclease activity;

(8) the detection probe has a resistance against 5' to 3' exonuclease activity;

(9) the detection probe has a backbone comprising a modification for resisting nuclease activity;

(10) the detection probe has a backbone comprising a modification selected from phosphorothioate ester bond, alkyl phosphotriester bond, aryl phosphotriester bond, alkyl phosphonate ester bond, aryl phosphonate ester bond, hydrogenated phosphate ester bond, alkyl phosphoramidate ester bond, aryl phosphoramidate ester bond, 2'-O-aminopropyl modification, 2'-O-alkyl modification, 2'-O-allyl modification, 2'-O-butyl modification, and 1-(4'-thio-PD-ribofuranosyl) modification; and

(11) the detection probe is labeled with a reporter group at its 5' end or upstream and labeled with a quencher group at its 3' end or downstream, or labeled with a reporter group at its 3' end or downstream and labeled with a quencher group at its 5' end or upstream; and

(12) the detection probes have the same reporter group, and the product in step (2) is subjected to melting curve analysis, and then the presence of the target nucleic acid is determined according to the melting peak in the melting curve; or, the detection probes have different reporter groups, and the product in step (2) is subjected to melting curve analysis, and then the presence of the target nucleic acid is determined according to the signal type of the reporter group and the melting peak in the melting curve.

15. The method according to claim 11, wherein steps (1) to (3) of the method are carried out by a protocol comprising the following steps (a) to (g):

(a) providing: (i) the sample containing the one or more target nucleic acids; (ii) the first universal primer and the second universal primer; and (iii) the target-specific primer pair and the detection probe for each target nucleic acid to be amplified;

(b) mixing the sample with the first universal primer, the second universal primer, the target-specific primer pair and the detection probe, and a nucleic acid polymerase;

(c) incubating the product of the previous step under a condition that allow nucleic acid denaturation;

(d) incubating the product of the previous step under a condition that allow nucleic acid annealing or hybridization;

(e) incubating the product of the previous step under a condition that allow nucleic acid extension;

(f) optionally, repeating steps (c) to (e) once or more times; and (g) performing melting curve analysis on the product of the previous step.

16. A primer set, which comprises: a first universal primer and a second universal primer, and, one or more target-specific primer pairs; wherein, the first universal primer comprises a first universal sequence;

the second universal primer comprises a second universal sequence, wherein the second universal sequence comprises the first universal sequence and additionally comprises at least one nucleotide at a 3' end of the first universal sequence;

each target-specific primer pair is capable of amplifying a target nucleic acid and comprises a forward primer and a reverse primer, wherein the forward primer comprises the first universal sequence and a forward nucleotide sequence specific to the target nucleic acid, and the forward nucleotide sequence is located at the 3' end of the first universal sequence; the reverse primer comprises the second universal sequence and a reverse nucleotide sequence specific to the target nucleic acid, and the reverse nucleotide sequence is located at a 3' end of the second universal sequence; and, the second universal sequence is not completely complementary to a complementary sequence of the forward primer.

17. The primer set according to claim 16, wherein the primer set has one or more technical features selected from the following:

(1) the first universal primer consists of the first universal sequence, or, the first universal primer comprises the first universal sequence and an additional sequence, and the additional sequence is located at a 5' end of the first universal sequence;

(2) the first universal sequence is located in a 3' portion of the first universal primer;

(3) the second universal primer consists of the second universal sequence, or, the first universal primer comprises the second universal sequence and an additional sequence, and the additional sequence is located at a 5' end of the second universal sequence;

(4) the second universal sequence is located in a 3' portion of the second universal primer;

(5) the second universal primer comprises the first universal sequence and additionally comprises 1-5, 5-10, 10-15, 15-20 or more nucleotides at the 3' end of the first universal sequence;

(6) in the forward primer, the forward nucleotide sequence is directly linked to the 3' end of the first universal sequence, or the forward nucleotide sequence is linked to the 3' end of the first universal sequence through a nucleotide linker;

(7) the forward primer further comprises an additional sequence, which is located at a 5' end of the first universal sequence;

(8) the forward primer comprises the first universal sequence and the forward nucleotide sequence from 5' to 3'; or, the forward primer comprises the first universal sequence, a nucleotide linker and the forward nucleotide sequence from 5' to 3'; or, the forward primer comprises an additional sequence, the first universal sequence and the forward nucleotide sequence from 5' to 3'; or, the forward primer comprises an additional sequence, the first universal sequence, a nucleotide linker and the forward nucleotide sequence from 5' to 3';

(9) the forward nucleotide sequence is located in a 3' portion of the forward primer;

(10) in the reverse primer, the reverse nucleotide sequence is directly linked to the 3' end of the second universal sequence, or the reverse nucleotide sequence is linked to the 3' end of the second universal sequence through a nucleotide linker;

(11) the reverse primer further comprises an additional sequence, which is located at a 5' end of the second universal sequence;

(12) the reverse primer comprises the second universal sequence and the reverse nucleotide sequence from 5' to 3'; or, the reverse primer comprises the second universal sequence, a nucleotide linker and the reverse nucleotide sequence from 5' to 3'; or, the reverse primer comprises an additional sequence, the second universal sequence, and the reverse nucleotide sequence from 5' to 3'; or, the reverse primer comprises an additional sequence, the second universal sequence, a nucleotide linker and the reverse nucleotide sequence from 5' to 3';

(13) the reverse nucleotide sequence is located in a 3' portion of the reverse primer;

(14) at least one nucleotide at the 3' end of the second universal sequence is not complementary to a complementary sequence of the forward primer;

(15) 1-5, 5-10, 10-15, 15-20 or more nucleotides at the 3' end of the second universal sequence is not complementary to a complementary sequence of the forward primer; and

(16) the primer set comprises 1-5, 5-10, 10-15, 15-20, 20-50 or more target-specific primer pairs.

18. A kit comprising the primer set according to claim 16, and one or more components selected from the following: a nucleic acid polymerase, a reagent for nucleic acid amplification, a reagent for sequencing, a reagent for gene chip detection, a reagent for melting curve analysis, or any combination thereof.

19. The kit according to claim 18, wherein the kit has one or more technical features selected from the following:

(1) the nucleic acid polymerase is a template-dependent nucleic acid polymerase;

(2) the reagent for nucleic acid amplification comprises a working buffer for enzyme, dNTPs, water, a solution containing ion, a single-stranded DNA-binding protein, or any combination thereof;

(3) the reagent for sequencing comprises a working buffer for enzyme, dNTPs, ddNTPs, water, a solution containing ion, a single-strand DNA-binding protein (SSB), a ligase, a nucleic acid linker, a sequencing primer, or any combination thereof;

(4) the reagent for gene chip detection comprises a working buffer for enzyme, dNTPs, water, a hybridization buffer, a washing buffer, a labeling reagent, or any combination thereof; and (5) the reagent for melting curve analysis comprises a detection probe.

* * * * *